US006696844B2

(12) United States Patent
Wong et al.

(10) Patent No.: US 6,696,844 B2
(45) Date of Patent: Feb. 24, 2004

(54) APPARATUS AND METHOD FOR REAL TIME DETERMINATION OF MATERIALS' ELECTRICAL PROPERTIES

(75) Inventors: Yee Chin Wong, Tucson, AZ (US); Andrea J. Yool, Tucson, AZ (US); Kristi A. Hansen, Tucson, AZ (US); Junius E. Taylor, Phoenix, AZ (US)

(73) Assignee: Engineering & Research Associates, Inc., Tucson, AZ (US)

( * ) Notice: Subject to any disclaimer, the term of this patent is extended or adjusted under 35 U.S.C. 154(b) by 93 days.

(21) Appl. No.: 09/944,421

(22) Filed: Aug. 31, 2001

(65) Prior Publication Data

US 2002/0068931 A1 Jun. 6, 2002

Related U.S. Application Data

(60) Provisional application No. 60/249,561, filed on Nov. 17, 2000, provisional application No. 60/249,471, filed on Nov. 17, 2000, provisional application No. 60/249,562, filed on Nov. 17, 2000, and provisional application No. 60/284,397, filed on Apr. 17, 2001.

(51) Int. Cl.[7] .................. G01R 27/08; G01R 27/26; A61B 18/18; A61B 5/053; G01N 27/02
(52) U.S. Cl. ............... 324/693; 324/663; 324/71.1; 606/42; 600/547
(58) Field of Search ............... 606/41, 34, 42–50, 606/38; 600/547, 506; 607/101, 102; 324/71.1, 639, 663, 637, 693; 307/87

(56) References Cited

U.S. PATENT DOCUMENTS

| 4,140,109 A | 2/1979 | Savic et al. ............... 128/2.1 Z |
| 4,641,649 A | 2/1987 | Walinsky et al. ......... 128/303.1 |
| 4,785,815 A | 11/1988 | Cohen ......................... 128/642 |

(List continued on next page.)

OTHER PUBLICATIONS

Hindricks, et al., "Radiofrequency coagulation of ventricular myocardium: Improved prediction of lesion size by monitoring catheter tip temperature", European Heart Journal (1989), vol. 10, pp. 972–984.

Haines, et al., "Observations on Electrode–Tissue Interface Temperature and Effect on Electrical Impedance During Radiofrequency Ablation of Ventricular Myocardium", Circulation (Sep. 1990), vol. 82, No. 3, pp. 1034–1038.

Blouin, et al., "Assessment of Effects of a Radiofrequency Energy Field and Thermistor Location in an Electrode Catheter on the Accuracy of Temperature Measurement", Pacing and Clinical Electrophysiology (May 1991), vol. 14, No. 5, Part I, pp. 807–813.

Langber, et al., "Temperature Monitoring During Radiofrequency Catheter Ablation of Accessory Pathways", Circulation, (Nov. 1992), vol. 86, pp. 1469–1474.

(List continued on next page.)

*Primary Examiner*—Anjan K. Deb
(74) *Attorney, Agent, or Firm*—Cahill, von Hellens & Glazer P.L.C.

(57) ABSTRACT

Apparatus for ablating organic material, such as tissue, during an EP procedure generates a monitor signal to provide unambiguous indicia of real time characteristics of the ablation site prior to, during and subsequent to the EP procedure by providing indicia representative of the impedance of the tissue along with indicia of the resistive and reactive components of the impedance. Inorganic materials, such as plastic, can be analyzed, welded or otherwise acted upon and the monitor signal will provide indicia representative of the real time characteristics of the material and change of character thereof. Application of the monitor signal alone can be used to determine the real time characteristics of either organic or inorganic materials to distinguish between healthy and abnormal or diseased tissue and to distinguish between similar inorganic materials having been subjected to different environments or conditions.

19 Claims, 15 Drawing Sheets

U.S. PATENT DOCUMENTS

| | | | |
|---|---|---|---|
| 4,869,248 A | | 9/1989 | Narula .................. 128/303.13 |
| 4,896,671 A | | 1/1990 | Cunningham et al. ...... 128/642 |
| 5,122,137 A | | 6/1992 | Lennox ........................ 606/40 |
| 5,280,429 A | * | 1/1994 | Withers ........................ 378/70 |
| 5,357,956 A | * | 10/1994 | Nardella ...................... 600/374 |
| 5,454,370 A | | 10/1995 | Avitall ......................... 128/642 |
| 5,456,682 A | | 10/1995 | Edwards et al. ............... 606/31 |
| 5,462,545 A | | 10/1995 | Wang et al. ................... 606/41 |
| 5,836,990 A | | 11/1998 | Li ............................... 607/28 |
| 5,872,456 A | * | 2/1999 | Roderick et al. ........... 324/637 |
| 5,928,159 A | * | 7/1999 | Eggers et al. ............... 600/547 |
| 6,066,139 A | | 5/2000 | Ryan et al. ................... 606/50 |
| 6,112,123 A | | 8/2000 | Kelleher et al. .............. 607/98 |
| 6,113,592 A | | 9/2000 | Taylor ......................... 606/34 |
| 6,123,702 A | | 9/2000 | Swanson et al. .............. 606/34 |
| 6,217,574 B1 | | 4/2001 | Webster ........................ 606/41 |

OTHER PUBLICATIONS

Strickberger, et al., "Relation between impedance and endocardial contact during radiofrequency catheter ablation", American Heart Journal (Aug. 1994), vol. 128, pp. 226–229.

He, et al., "Temperature Monitoring During RF Energy Application Without the Use of Thermistors or Thermocouples", (Abstract No. 244), Pacing and Clinical Electrophysiology (Apr. 1996), vol. 19, Part II, p. 626.

Mackey, et al., "Simultaneous Multipolar Radiofrequency Ablation in the Monopolar Mode Increases Lesion Size", Pacing and Clinical Electrophysiology (1996), vol. 19(7), pp. 1042–1048.

He, et al., "In Vivo Experiment of Radiofrequency (RF) Energy Application Using Bio–battery–induced Temperature Monitoring", (Abstract No. 913–123), Journal of American Coll Cardiol (Feb. 1997), vol. 29, pp. 32A.

Avitall, et al., "The Effects of Electrode–Tissue Contact on Radiofrequency Lesion Generation", Pacing and Clinical Electrophysiology (Dec. 1997), vol. 20, Part I, pp. 2899–2910.

Hammill, et al., "The Rapidly Changing Management of Cardiac Arrhythmias", Am J Respir Crit Care Med (2000), vol. 161, pp. 1070–1073.

Matsudaira, et al., "Highly Sensitive Impedance Monitoring May Predict Electrode Contact Pressure and Lesion Size During Radiofrequency Ablation Using A Saline Irrigated Catheter", (poster), NASPE (May 2001), [online], [retrieved on Oct. 1, 2001]. Retrieved from NAPSE Database.

"Basic Electrochemistry", Chapter 1.3, Modern Electrochemistry, John O'M. Bockris, published by Plenum Press, New York, dated 1970, pp. 12–31.

"Reversible Electrode Potentials", Chapter IV, Electrochemistry Principles and Applications, by Edmund C. Potter, published by Cleaver–Hume Press, Ltd., dated 1956, pp. 73–100.

"Electrodes and Electrochemical Cells", Chapter 4, Introduction to Electrochemistry, by D. Bryan Hibbert, published by MacMillan Press Ltd., dated 1993, pp. 59–89.

"Reversible Cells", Chapter XII, Electrochemistry of Solutions, by S. Glasstone, published by Methuen & Co. Ltd., London, dated 1937 (Second Edition), pp. 282–311.

Abst #22—"Tip Temperature is not an Indicator of Intramyocardial Temperatures During Radiofrequency Catheter Ablation", Pacing and Clinical Electrophysiology, NASPE Abstracts & Program, Apr. 1995, vol. 18, #4, Part II, p. 801.

Abst #145–"Radiofrequency Catheter Ablation Using A Saline Irrigated Electrode in Patients with Prior Failed Accessory Pathway Ablation", Pacing and Clinical Electrophysiology, NASPE, Apr. 1995, Vol 18, 190 4, Part II, p. 832.

"HeadsUP" brochure "EPT–1000 Cardiac Ablation System: The Ablation Technology You Need Today . . . ", EP Technologies Inc., Sunnyvale, California, dated 10/94, (five pages).

"HeadsUp" brochure "ATAKR™: Radio Frequency Ablation System", CardioRhythm, San Jose, California, dated 2/95, (three pages).

Flyer "HAT 200 S: Radio Frequency System for Ablation, Recanalization and Angioplasty", Baylis Medical Company Inc., Montreal, Canada, (four pages).

"Surgical Treatment of Cardiac Arrhythmias", by Alden H. Harken, Scientific American, Jul. 1993, pp. 68–74.

"The Biophysics of Radiofrequency Catheter Ablation in the Heart: The Importance of Temperature Monitoring", by David E. Haines, PACE, vol. 16, Mar. 1993 (Part II), pp. 586–591.

"Basic Aspects of Radiofrequency Catheter Ablation", by Sunil Nath M.D. et al., Journal of Cardiovascular Electrophysiology, vol. 5, No. 10, Oct. 1994, pp. 863–876.

"Biophysics and Pathology of Catheter Energy Delivery Systems", by Sunil Nath and David Haines, Progress in Cardiovascular Diseases, vol. XXXVII, No. 4, Jan./Feb. 1995, pp. 185–204.

"Physics and Engineering of Transcatheter Cardiac Tissue Ablation", by Boaz Avitall, M.D. et al., JACC, vol. 22, No. 3, Sep. 1993, pp. 921–932.

"Impedance Monitoring During Radiofrequency Catheter Ablation in Humans", by Mark Harvey et al., PACE, vol. 15, Jan. 1992, pp. 22–27.

"Simultaneous Multipolar Radiofrequency Ablation in the Monopolar Mode Increases Lesion Size", by Sean Mackey et al., Pace, Jun. 1995 (in press), pp. 1–15.

"Catheter ablation of accessory AV pathways (Wolff–Parkinson–White Syndrome) by radiofrequency current", by W. Jackman, et al., N. Engl J. Med 1991;324:1605–1611.

"Diagnosis and cure of the Wolff–Parkinson–White Syndrome or paroxysmal supraventricular tachycardias during a single electrophysiology test", by Calkins et al., N. Engl J. Med 1991:324:1612–1618.

"Radiofrequency current catheter ablation of accessory atrioventricular pathways", by Kuck et al., Lancet 1991:337:1557–1561.

"Curative percutaneous catheter ablation using radiofrequency energy for accessory pathways in all locations: Results in 100 consecutive patients", by Lesh et al., J. Am Coll Cardiol 1992; 19:1303–1309.

"Catheter modification of the atrioventricular junction with radiofrequency energy for control of atrioventricular nodal reentry tachycardia", by Lee, et al., Circulation 1991;83:827–835.

"Treatment of supraventricular tachycardia due to atrioventricular nodal reentry by radiofrequency catheter ablation of slow pathway conduction", by W. Jackman, et al., N. Eng J. Med 1992;327:313–318.

"Selective radiofrequency ablation of the slow pathway for the treatment of atrioventricular nodal reentrant tachycardia. Evidence for involvement of perinodal myocardium within the reentrant circuit", by Kay, et al.,Circulation, 1992, 85(5): 1675–88.

"Selective transcatheter ablation of the fast and slow pathways using radiofrequency energy in patients with atrioventricular nodal reentry tachycardia", Jazayeri, et al., *Circulation*, 1992;85:1318–1328.

"Radiofrequency catheter ablation of ventricular tachycardia in patients without structural heart disease", by L. Klein, et al., *Circulation* 1992;85:1666–1674.

"Radiofrequency catheter ablation of idiopathic left ventricular tachycardia guided by a Purkinje potential", by Nakagawa, et al. *Circulation*, 1993;88:2607–2617.

"The use of bio–battery cell output to predict lesion formation and prevent rapid impedance rise", by P. Sharma, et al., (abstract), *J. Am Coll Cardiol*, 1998;31:159A.

*Fundamentals of Electrochemistry*, entitled basic Concepts of Theoretical Electrochemistry by VS Bagotzky, pp. 1–103, Plenum Press, New York, 1993.

*High–Energy Non–Aqueous Batteries*, by A. Cisak and L. Werblan, Chapter 2 entitled "Theoretical Principles of Action of Galvanic Cell", pp. 20–38, Ellis Horwood, NY 1993.

*Physical Electrochemistry: Principles, Methods and Applications*, pp. 1–25, Chapter 1, entitled "Fundamentals of Physical Electrochemistry" edited by Israel Rubinstein, Marcel Dekker, Inc., 1995.

"Temperature measurement as a determinant of tissue heating during radiofrequency catheter ablation: an examination of electrode thermistor positioning for measurement accuracy", by ID McRury, et al., *J. Cardiovasc Electrophysiol* 1995;6(4):268–78.

"Influence of flow on intratissue temperature in radiofrequency catheter ablation", by S. Runbrecht, et al., (abstract) *Circulation* 1997;96(8): 1–143.

"Predictive parameters of electrode–tissue contact in vivo prior to and during radiofrequency energy application", by D.S. He, et al., (abstract) *Circulation* 1997;96(8):1–143.

"Usefulness of measuring the bioimpedance for predicting the efficiency of heating during radiofrequency catheter ablation", by SKS Huang, et al., (abstract) *Circulation*, 1997;96(8):1–143.

"Transmural ablation of the atrial tissue using an irrigated tip electrode with monitoring the electrogram at the ablation site", by S. Satake, et al., (abstract), *Circulation* 1997;96(8):1–576.

"Comparison of in vivo tissue temperature profile and lesion geometry for radiofrequency ablation with a saline–irrigated electrode versus temperature control in a canine thigh muscle preparation", by H. Nakagawa, et al., *Circulation* 1995;91(8):2264–73.

\* cited by examiner

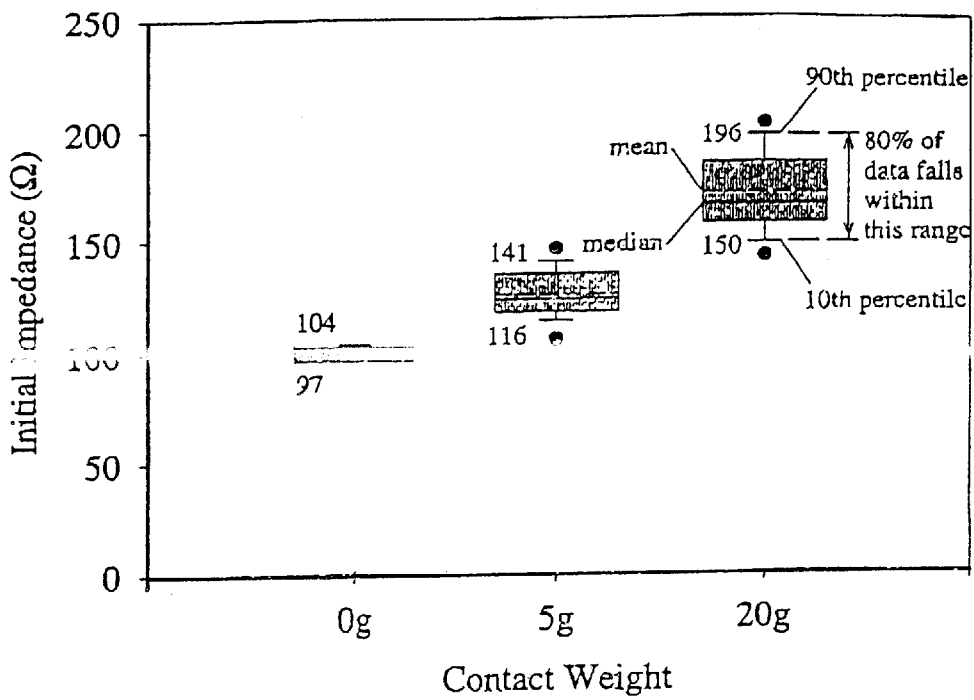
Figure 6a  Initial Impedance vs. Contact Weight
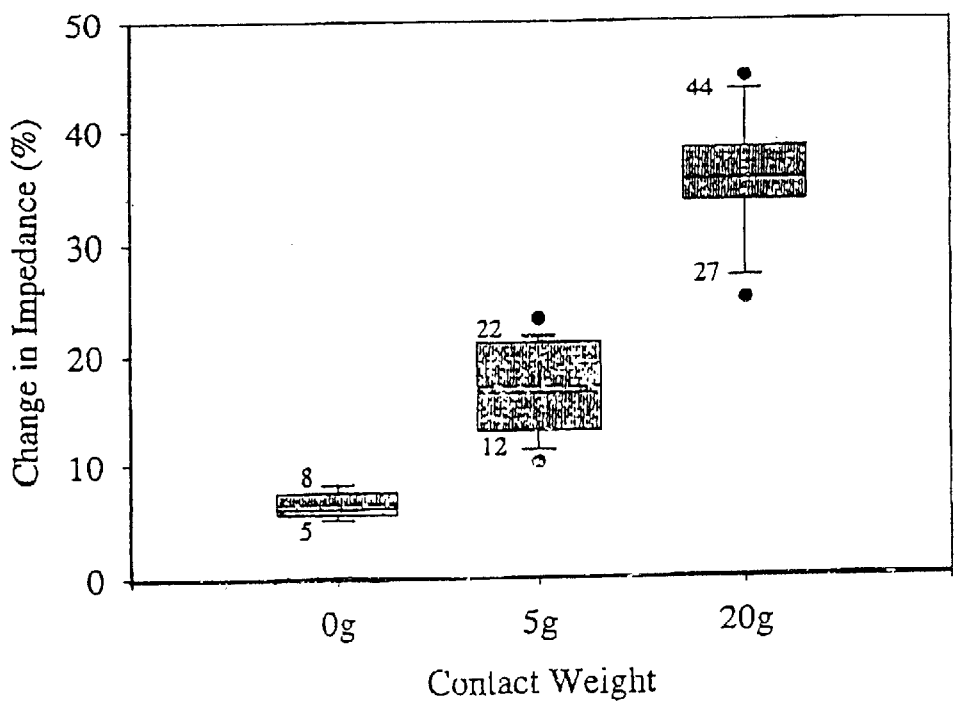
Figure 6b  Change in Impedance vs. Contact Weight

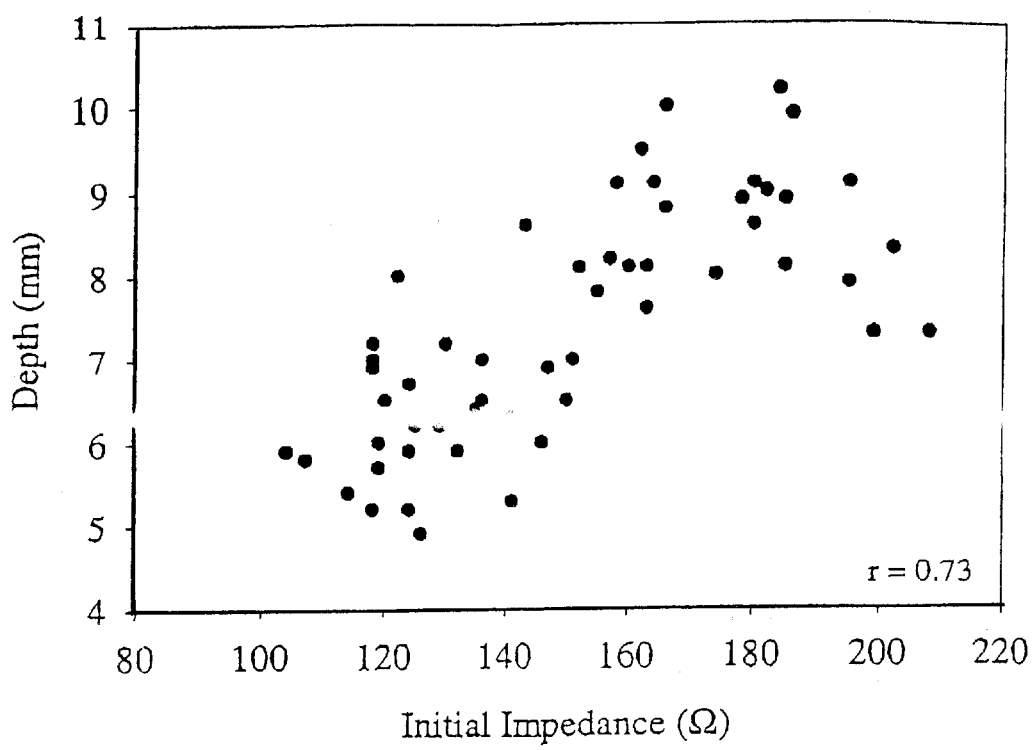
Figure 7a  Initial Impedance vs. Depth
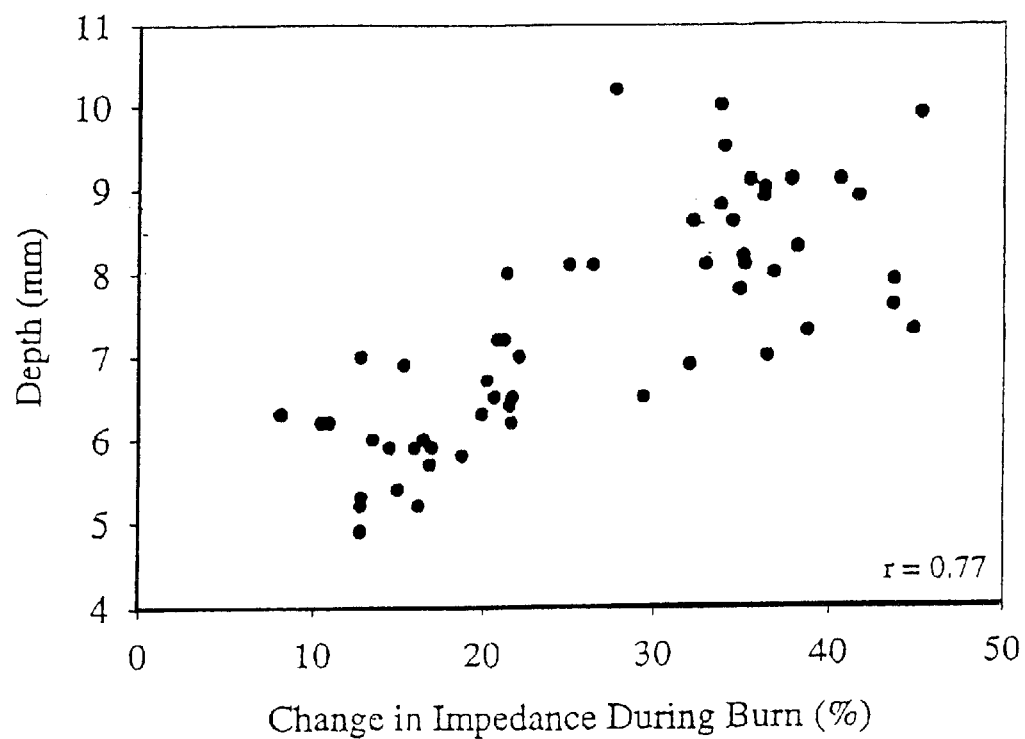
Figure 7b  Change in Impedance vs. Depth

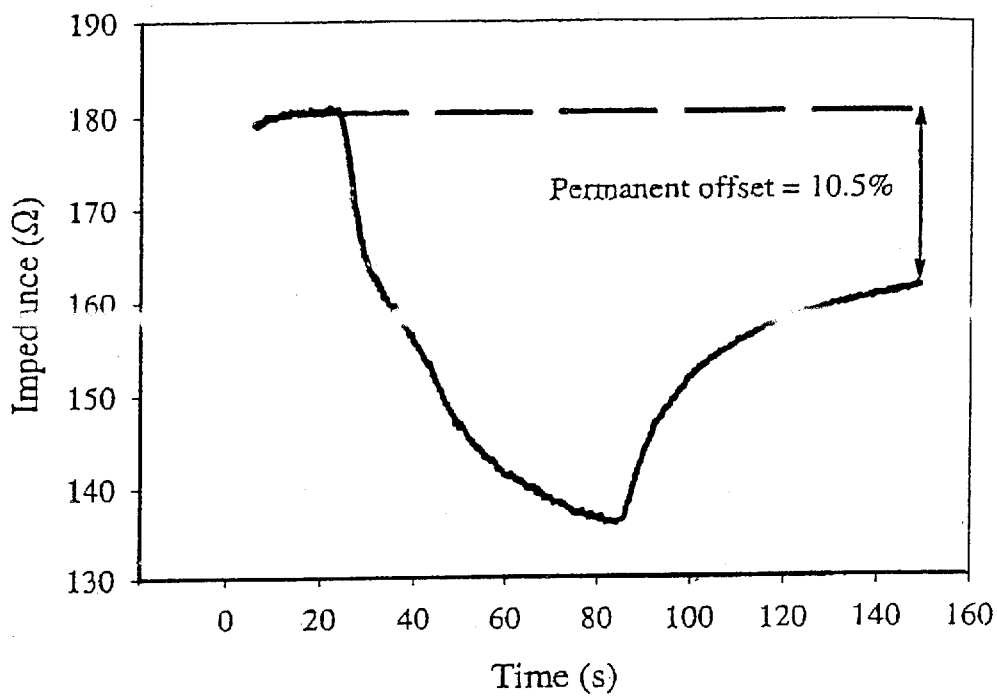
Figure 8a  Permanent Offset in Impedance
*in vitro*, Lesion Depth = 3.7 mm
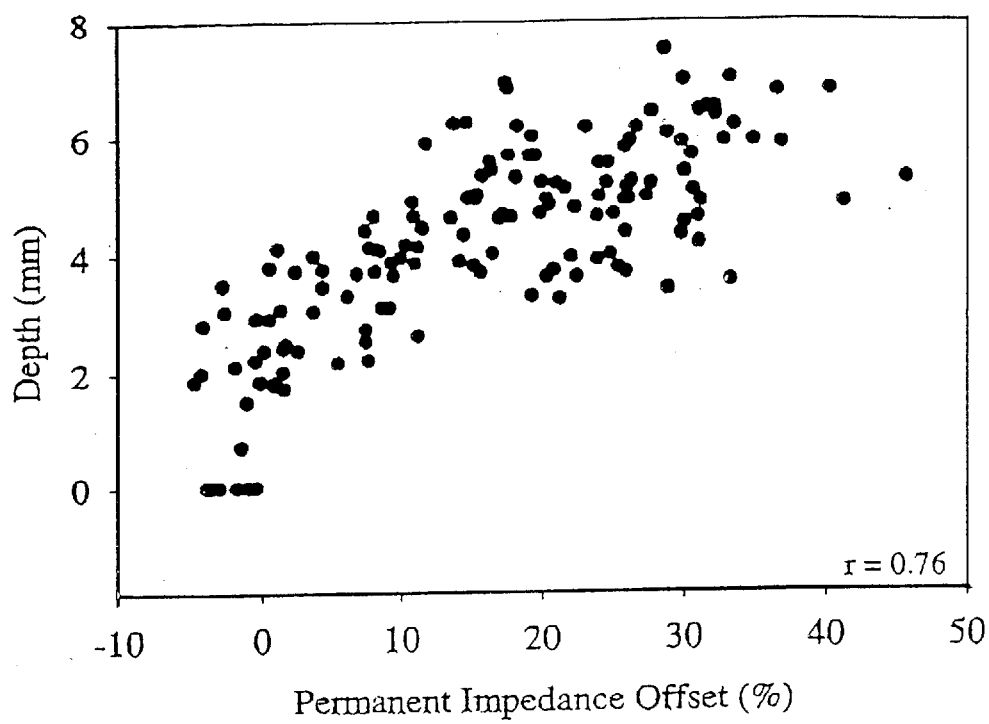
Figure 8b  Permanent Offset vs. Depth

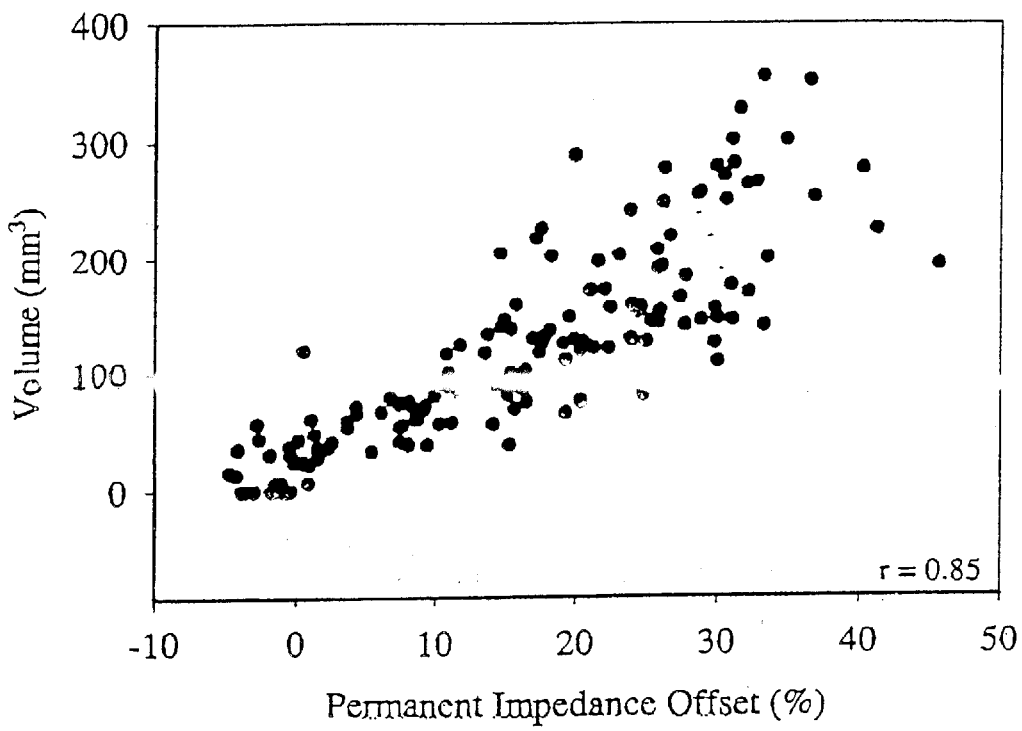
Figure 8c  Permanent Offset vs. Volume
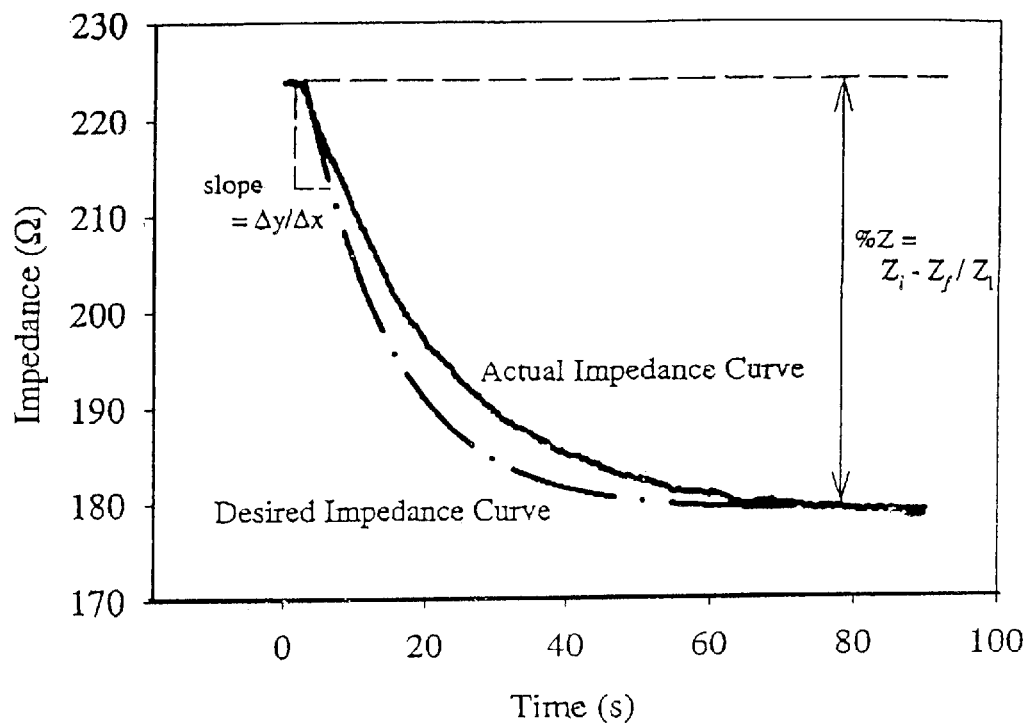
Figure 9a  Impedance Control Curve vs. Actual Impedance Curve Figure 9b  Lesion Depth vs % Change in Impedance
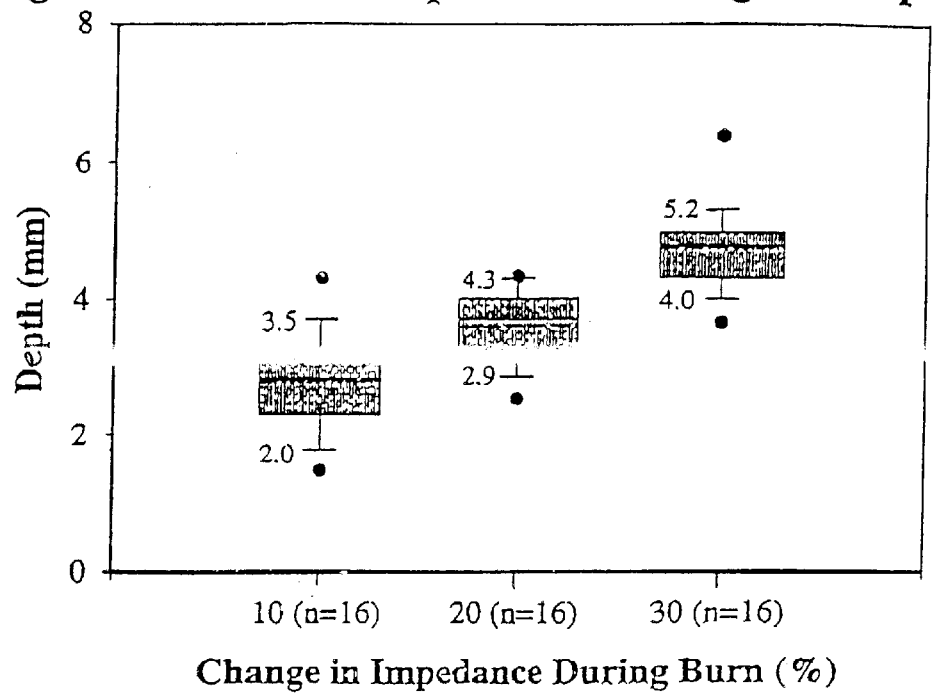
Figure 9c  Lesion Volume vs % Change in Impedance
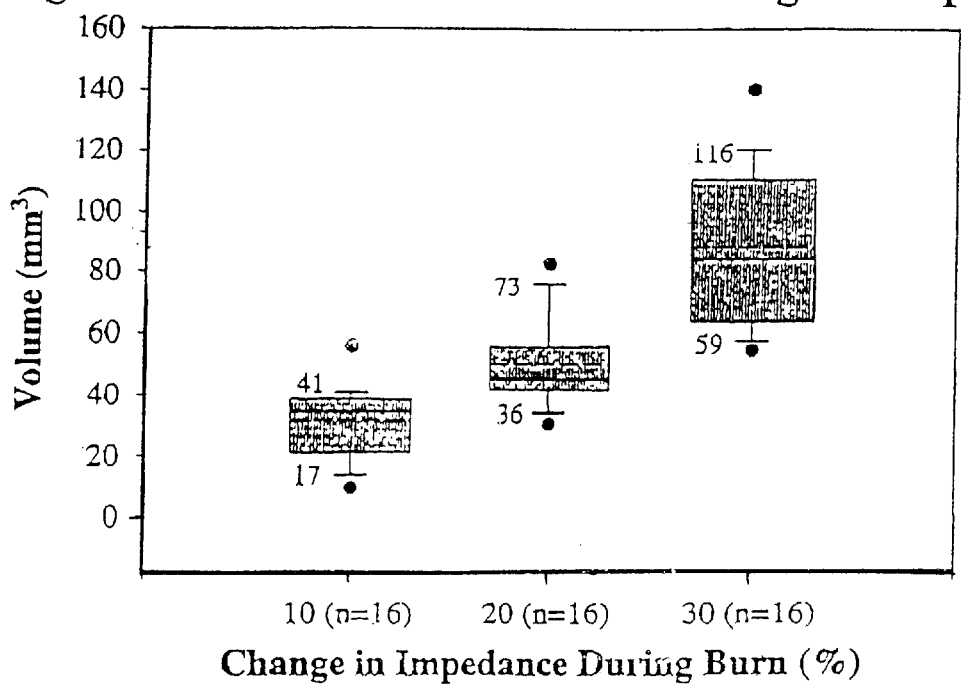

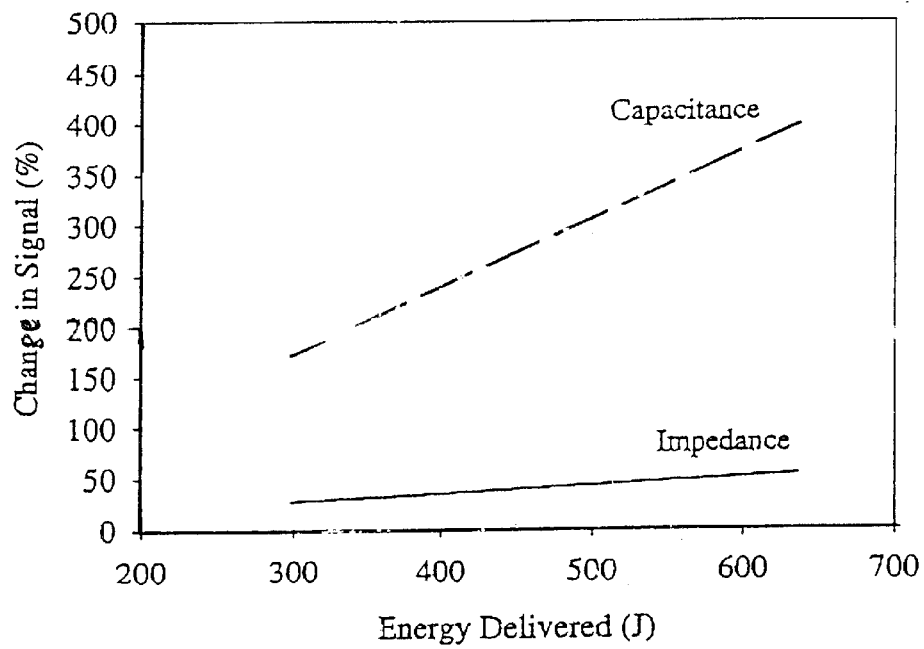
Figure 10a Comparison of Change in Capacitance to Change in Impedance at Thermal Equalibrium Before and After Lesion Formation vs. Energy Delivered
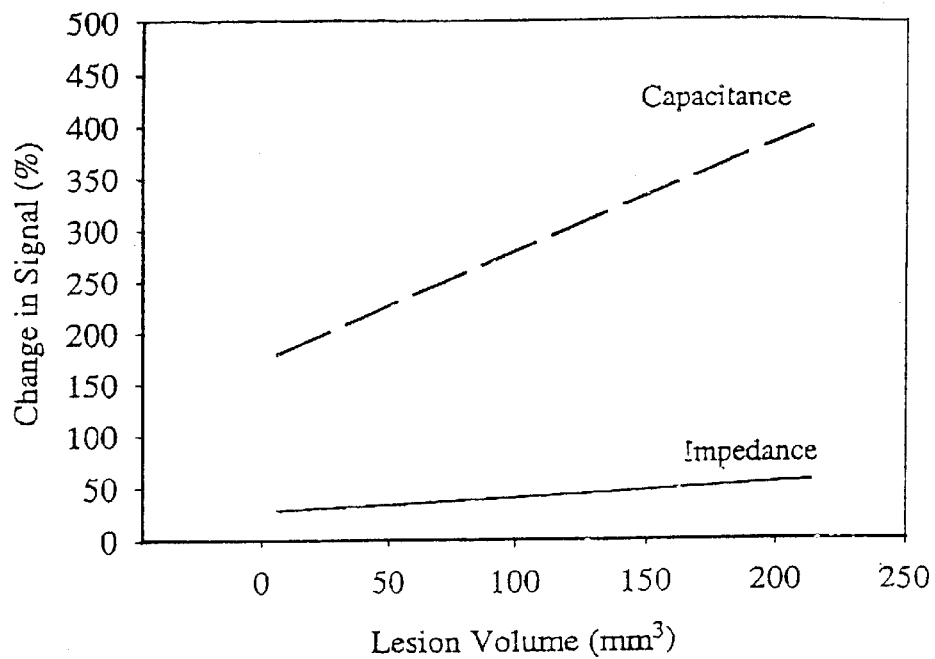
Figure 10b Comparison of Change in Capacitance to Change in Impedance at Thermal Equalibrium Before and After Lesion Formation vs. Lesion Volume

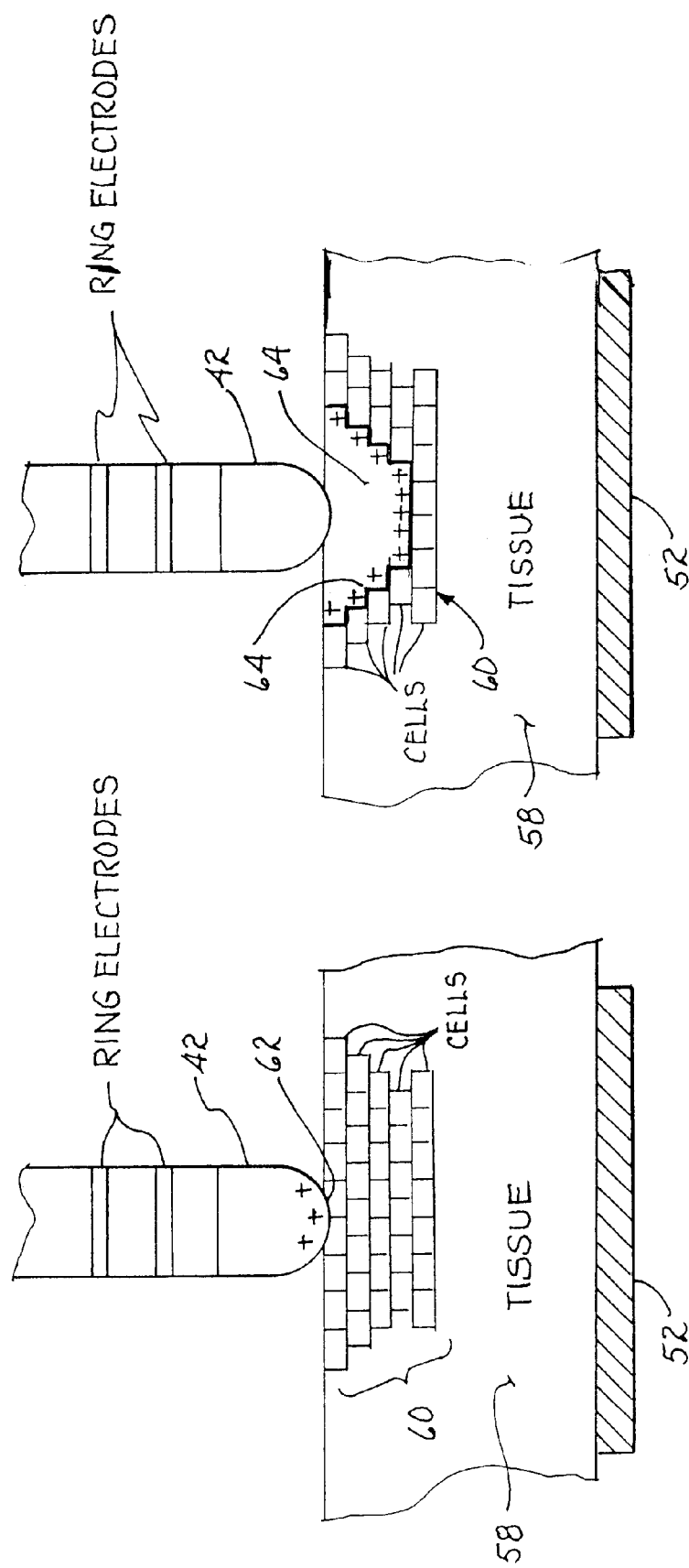

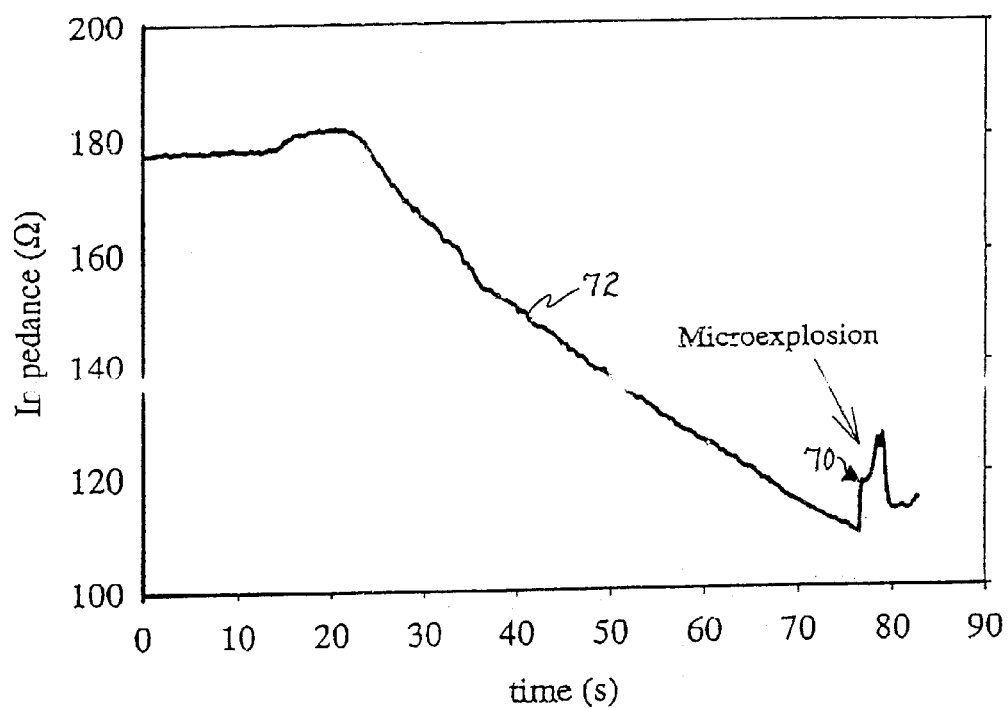
Figure 12: Impedance Curve During a Microexplosion

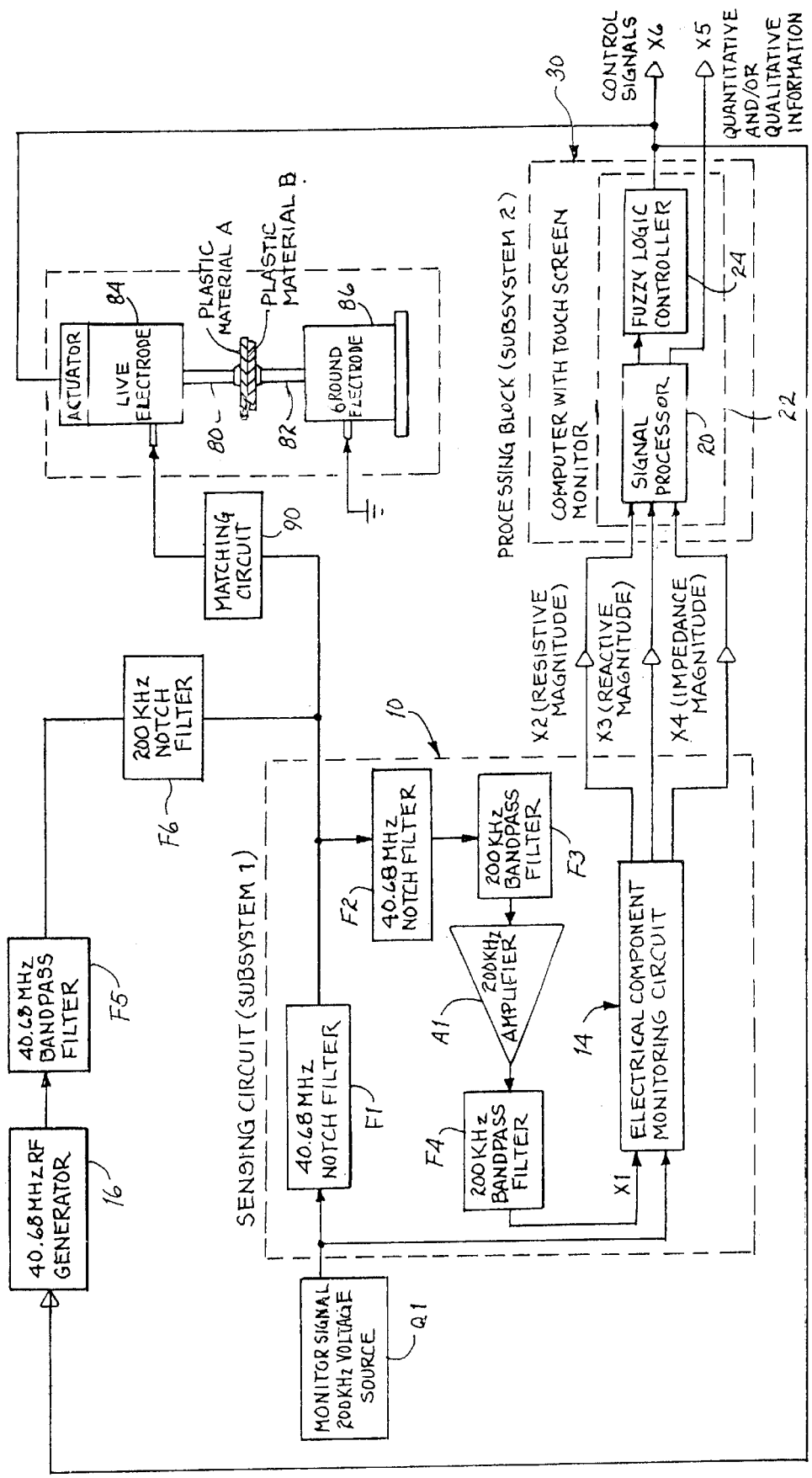
Fig. 13 INDUSTRIAL RF WELDING SYSTEM

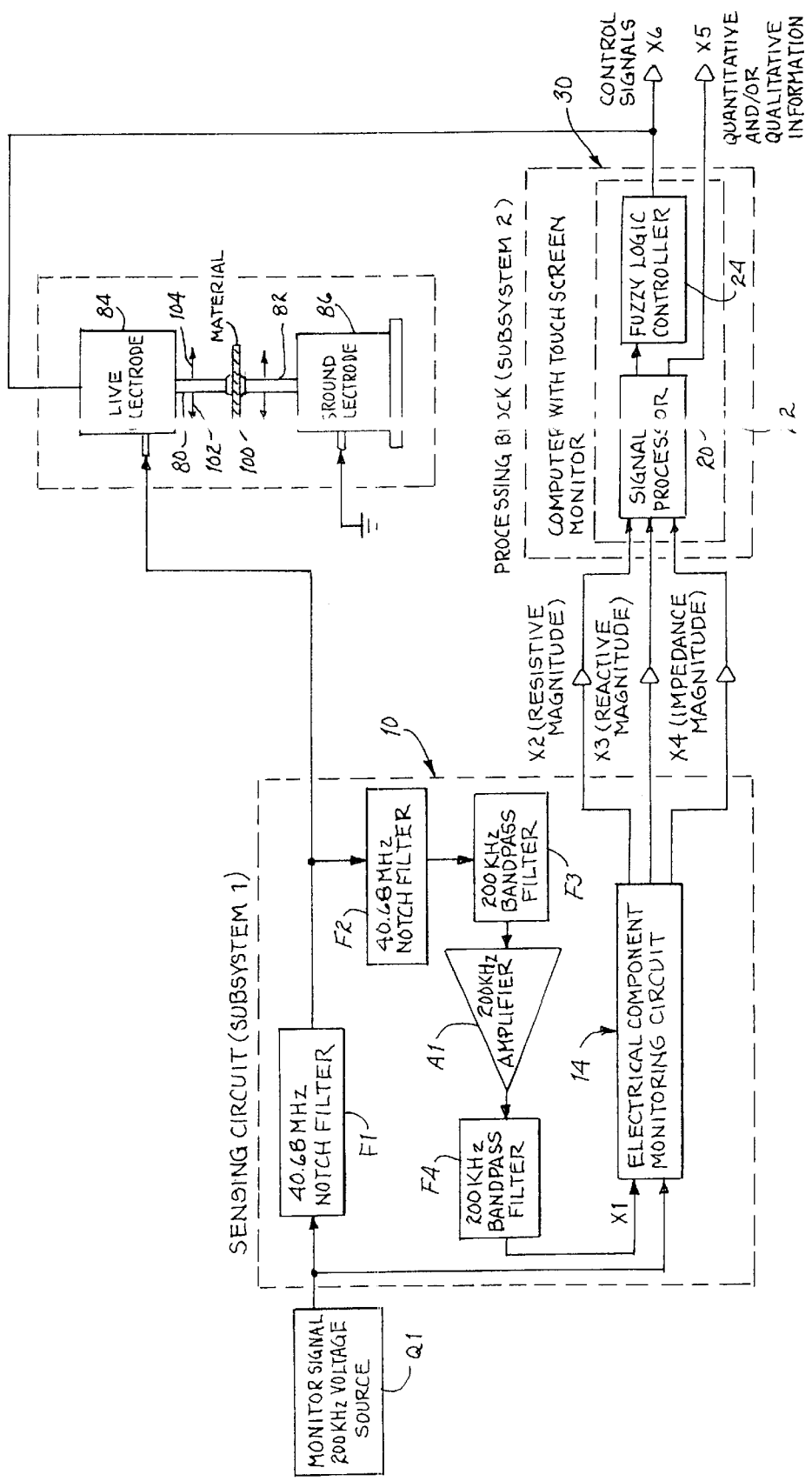
Fig. 14 APPARATUS FOR MATERIAL ANALYSIS

APPARATUS AND METHOD FOR REAL TIME DETERMINATION OF MATERIALS' ELECTRICAL PROPERTIES

CROSS-REFERENCE TO RELATED APPLICATION

The present application includes and claims priority to a disclosure contained in the provisional applications entitled "CAPACITANCE MEASUREMENT DURING TISSUE ABLATION", assigned Serial No. 60/249,561, filed Nov. 17, 2000, "SENSITIVE IMPEDANCE SIGNAL MEASUREMENT DURING TISSUE ABLATION" assigned Serial No. 60/249,471, filed Nov. 17, 2000; and "FUZZY LOGIC" assigned Serial No. 60/249,562, filed Nov. 17, 2000, and "METHOD FOR PREDICTING ABLATION FROM CATHETER TO TISSUE PRESSURE", assigned Serial No. 60/284,397, filed Apr. 17, 2001 and includes subject matter disclosed in provisional applications entitled "QUANTITATIVE CHARACTERISTICS OF TISSUE BIO-CONDUCTANCE AND LESION FORMATION" assigned Serial No. 60/137,589, filed Jun. 4, 1999; "CHANGE IN TISSUE COMPONENT OF MYOCARDIAL LESION DEPTH" assigned Serial No. 60/205,313, filed May 18, 2000; "BIOCONDUCTANCE CORRELATES WITH TISSUE TEMPERATURE IN VITRO" assigned Serial No. 60/205,312, filed May 18, 2000; "EFFECTS OF DIFFERENT PERFUSION RATES ON INTRA-MYOCARDIAL RATES" assigned Serial No. 60/205,311, filed May 18, 2000; "EFFECTS OF REDUCING CATHETER DISTAL ELECTRODE LENGTH" assigned Serial No. 60/205,309, filed May 18, 2000; "FUZZY AND IMPEDANCE CONTROL" assigned Serial No. 60/211,043, filed Jun. 12, 2000; all of which applications are assigned to the present assignee.

BACKGROUND OF THE INVENTION

1. Field of the Invention

The present invention relates to apparatus and methodology for electronically determining the qualitative and quantitative physical state, in real time, of either inorganic and organic materials by monitoring their electrical properties for data acquisition, manipulation, analysis and system control.

2. Background of the Invention

Radio frequency (RF) generators used in tissue ablation medical procedures provide RF energy between one or more electrodes supported on an ablation catheter and a ground electrode applied to the patient; alternatively, the catheter may include one or more rings or other electrode(s) that serve in the manner of a ground electrode. The temperature of the catheter obtained from a thermocouple or thermistor embedded in the electrode tip of the catheter is usually used to control the delivery of ablation energy. While such a thermocouple/thermistor measurement may be sufficiently accurate to reflect the temperature of the catheter tip electrode, it is inherently inaccurate and imprecise in determining the temperature of the tissue during ablation (Hindricks, et. al., "Radiofrequency coagulation of ventricular myocardium: Improved prediction of lesion size by monitoring catheter tip temperature", Eur Heart Journal 1989; 10:972–984; Langberg et. al., "Temperature monitoring during radiofrequency catheter ablation of accessory pathways", Circulation 1992;86:1469–1474; Haines et. al., "Observation on electrode-tissue interface temperature and effect on electrical impedance during radiofrequency ablation of ventricular myocardium", Circulation 1990;82:1034–1038; Blouin, et. al, "Assessment of effects of radiofrequency energy field and thermistor location in an electrode catheter on the accuracy of temperature measurement", PACE 1991; Part I 14:807–813.). Because of the thermocouple's (thermistor's) inability to accurately reflect tissue temperature, there is a propensity to overheat the ablation site, which could lead to four potentially injurious conditions (He, et. al., "Temperature monitoring during RF energy application without the use of the thermistors or thermocouples", (abstract) PACE 1996; 19:626; He, et. al., "In vivo experiments of radiofrequency (RF) energy application using bio-battery-induced temperature monitoring", (abstract) J. Am Coll Cardiol 1997; 29:32A). First, the delivery of RF energy from the catheter tip may become ineffective due to blood coagulation, and furthermore, the coagulum can be dislodged into the blood stream potentially causing a stroke due to occlusion of downstream blood vessels in critical organs. Second, overheated tissue at the ablation site may "stick to" the catheter tip and result in tearing of the tissue upon removal of the catheter. Third, inadequate tissue temperature control can result in unnecessary injury to the heart, including perforation. Fourth, extreme heating of the tissue can cause one or more micro-explosions, which micro-explosions are undesirable since they may displace a piece of tissue into the blood stream and possibly cause a stroke. Because of these potentially dangerous conditions, an apparatus for accurately determining, on a real time basis, the state of tissue during ablation would be of great advantage in performing medical electrophysiological (EP) procedures. Furthermore, if prevention of micro-explosions is not possible for any reason, perhaps due to tissue abnormalities, it would also be advantageous if the apparatus would identify the occurrence of a micro-explosion(s) so that the patient can be closely monitored for adverse reaction during and after the procedure.

Another factor that complicates a cardiac EP procedure in a dynamic beating heart with blood flow is the quality of the electrode-tissue contact. The main aim of an EP procedure is to damage a selected site on cardiac tissue to interrupt errant electrical pulses that cause arrhythmias. To ensure a successful EP procedure, consistent and reliable lesion creation is needed. However, in order to create lesions in a consistent and reliable manner, it is necessary to have good physical contact between the active catheter electrode and the tissue surface. Prior art generators (such as ultrasound, RF, and cryogenic generators) include no device or mechanism that provides adequate information on the quality of electrode-tissue contact. Methods used by cardiologists to determine contact include monitoring the ECG injury current signal before and during energy delivery, monitoring tissue impedance and electrode temperature during energy delivery. (Strickberger, et. al., "Relation between impedance and endocardial contact during radiofrequency catheter ablation", American Heart Journal 1994; 128:226–229; Avitall, et. al., "The effects of electrode-tissue contact on radiofrequency lesion generation", PACE 1997; 20:2899–2910). The prior art technology for determining the quality of the electrode-tissue contact is inefficient and ineffective for various reasons. First, because the contact impedance can only be faintly determined during the delivery of energy, this approach unnecessarily lengthens the duration of the procedure. To help illustrate this point, consider the following presently practised methodology. A physician first has to maneuver the catheter with the aid of a fluoroscope to the site on the tissue to be ablated. The physician would then have to deliver a small dose of RF energy so that the change in temperature or impedance signals can be monitored for approximately 30 to 40 seconds. If the monitored signals do not indicate sufficient contact, the whole process would have to be repeated until sufficient contact was achieved. This repetitive process also subjects the patient to unnecessary exposure to radiation from the fluoroscope. Second, the difference between poor contact (i.e. catheter electrode lightly touching the tissue) and good contact (i.e. catheter electrode firmly in contact with tissue) is of insufficient resolution due to inadequate sensitivity of the impedance measurements in prior art RF generators. One prior art RF generator typically provides an approximate initial impedance of 113±16Ω (mean ±SD) for poor contact and 139±24Ω for good contact (Strickberger, et. al., "Relation between impedance and endocardial contact during radiofrequency catheter ablation", American Heart Journal 1994; 128:226–229). The approximate changes in impedance during a short ablation with another prior art generator (40 second application of 20 W of RF energy) are 14±10Ω for poor contact and 20±2Ω for good contact (Avitall, et. al., "The effects of electrode-tissue contact on radio frequency lesion generation", PACE 1997; 20:2899–2910). These data show that the difference in the initial impedance (measured during short duration low energy delivery) that is used to estimate good contact is only 26Ω and the large standard error makes this measurement uncertain since there is substantial overlap in the values measured. In the second example the difference in the change of impedance (during ablation) is only 6Ω. Third, the technique using the change in temperature for estimating contact pressure can not be used effectively with an irrigated or chilled catheter since the electrode of the catheter is intentionally not responsive to increases in tissue temperature, unlike a non-cooled catheter. Due to the above reasons, cardiologists find these existing approaches of determining contact quality cumbersome and inefficient, and usually skip the process. Thus, an apparatus capable of effectively monitoring and providing accurate and sensitive tissue impedance measurement before, during, and after an EP procedure as well as quantifying with sufficient resolution the contact quality for discriminating between no, poor, fair, and good electrode-tissue contact would be of great utility and advantage in performing an EP procedure.

Catheter ablation treatment of atrial fibrillation often requires the formation of linear lesions and/or circumferential lesions and treatment of ventricular tachycardia typically requires formation of deep lesions. If tissue lesion formation below an electrode could be accurately monitored, it could improve the ability to produce a continuous line of lesions required for some ablation treatments of atrial fibrillation. Additionally, accurate monitoring could provide an indication of successful lesion formation for treatment of ventricular tachycardia. Thus, an apparatus and a method for monitoring lesion formation, size and depth, features not provided by prior art generators, would be of great advantage.

A similar need for real-time monitoring of inorganic materials is present in many industrial applications. RF welding, for example, typically requires two plastics or metals to be heated and permanently joined. However, not all materials can be electrically heated efficiently or within practical limits. For example, no amount of electrical energy can weld two purely reactive plastics and attempting to weld purely reactive materials could result in expensive damage to the welding system. Therefore, an apparatus that can quantify and qualify the weldability of inorganic materials in real time would be of immense utility.

Implementing a system efficiently requires electrical matching for optimal energy consumption. For example, an unmatched RF heating and welding system requires more available power than a matched RF heating and welding system due to significant reflection of applied energy. This implies that implementation of a design using an unmatched RF welding system would not only be more expensive, due to the expensive higher power components as well as the higher energy consumption, but also more complex since heat compensation and management would become important. Electrical mismatch occurs for a variety of reasons, including changes in the properties of a material due to its chemical formulation, storage environment, aging, and during heating. An apparatus that monitors the electrical properties of a material in real time prior to and during heating or welding would allow an operator to manually, or allow the apparatus to automatically, tune the matching circuit to achieve and sustain optimal matching for increased energy consumption efficiency and for protecting the system from damage.

SUMMARY OF THE INVENTION

The present invention analyzes and/or treats organic or inorganic material and produces one or more outputs and may include one or more subsystems. The function of a first subsystem is to measure the electrical properties of the material and present these properties as inputs to a second subsystem. The electrical properties may be measured at an appropriate frequency or frequencies (for the purpose of demonstrating the implementation and application of the invention, a 50 KHz monitoring signal for an RF ablation system has been presented). A change in the current of the monitoring signal is reflective of a change in the state and properties of the material. The output signals of the first subsystem include measurement of the magnitude of the resistive component, the magnitude of the reactive component, and the impedance magnitude, all being measured across the material being analyzed or treated. The function of the second subsystem is to process these output signals, either individually or in combination, in digital or analog fashion, and to provide a quantitative measure of the property or state of the material for analysis and/or control purposes. The output of the second subsystem provides quantitative and/or qualitative signals and control signals. The quantitative and/or qualitative signals are signals for quantifying and/or qualifying events such as contact quality, lesion formation, etc., while the control signals are used for control purposes.

The present invention can be used for monitoring and controlling treatment of tissue during a cardiac electrophysiology ablation procedure, during procedures for heating or freezing of cancerous tumors, during procedures for management of spinal pain, and for other medical therapeutic procedures by providing accurate real time measurements of the impedance and the resistive and reactive electrical components of the tissue by exploiting real time electrical parameters as described herein. Alternatively, the present invention can be used to characterize plastic for quality control and to measure the quality of plastic forming and welding and in other medical and industrial applications.

It is therefore a primary object of the present invention to provide accurate and sensitive measurements of the resistive component, the reactive component, and the impedance of either organic or inorganic material in real time before, during, and after application of energy.

Another object of the present invention is to provide apparatus for verifying, assuring, and qualitatively and quantitatively assessing real time electrode-tissue contact to present information during an EP procedure before, during, and after the application of energy.

Yet another object of the present invention is to provide apparatus for monitoring and producing real time information that can be correlated with as well as qualifying and quantifying lesion volume and depth and also estimating tissue temperature.

Still another object of the present invention is to provide apparatus to safely control lesion depth and volume and tissue temperature to user specified values during an EP procedure.

Still another object of the present invention is to provide apparatus to detect tissue micro-explosions or other events such as slippage of a catheter during an EP ablation procedure.

Still another object of the present invention is to provide apparatus for producing signals reflective of differentiation between healthy and damaged tissue (such as infarct tissue), between different tissue types and textures, and discriminating between healthy tissue and adjacent unhealthy tissue (such as a tumor).

A yet further object of the present invention is to provide apparatus for producing a signal providing measurement of a material's electrical properties and any variation caused by the storage environment or age and differentiation between similar materials of different chemical formulation or age.

A yet further object of the present invention is to provide apparatus for producing a signal for preventing arcing during welding by identifying the existence of an air gap caused by missing, imperfect, or defective material and identifying the existence of inclusions or the presence of foreign matter on the surface of the material.

A yet further object of the present invention is to provide apparatus for identifying and quantifying electrically modifiable materials (such as RF responsive plastics) and accurately measuring the electrical properties of the materials for manual or automatic adjustment of a matching circuit to increase the energy efficiency of the apparatus.

A yet further object of the present invention is to provide apparatus for generating a signal useful for estimating and controlling the temperature of a material and/or change in temperature during a heating and welding process.

A still further object of the present invention is to provide apparatus for generating a signal determinative of a weld formed and the quality of the weld.

A still yet further object of the present invention is to provide a method for monitoring and controlling treatment of tissue during an ablation procedure.

A still further object of the present invention is to provide a method for distinguishing between healthy and abnormal or diseased tissue.

A still further object of the present invention is to provide a method for determining electrical properties of organic and inorganic materials.

A still further object of the present invention is to provide a method for determining the quality of the contact between an energy transmitting electrode and an underlying material prior to transmission of energy to modify the material.

A still further object of the present invention is to provide a method for generating control signals to permit control of the power and/or duration of energy transmission to an organic or inorganic material.

These and other objects of the present invention will become apparent to those skilled in the art as the description thereof proceeds.

BRIEF DESCRIPTION OF THE DRAWINGS

The present invention may be described with greater specificity and clarity with reference to the following drawings, in which:

FIG. 6a illustrates a graph demonstrating the change in initial impedance for different contact weights;

FIG. 6b illustrates the change in impedance during ablation for different contact weights;

FIG. 7a illustrates a graph correlating initial impedance to lesion depth;

FIG. 7b illustrates a graph correlating the change in impedance during ablation to lesion depth;

FIG. 8a illustrates a graph of the permanent offset associated with the impedance signal;

FIG. 8b illustrates a graph correlating lesion depth to permanent impedance offset;

FIG. 8c illustrates a graph correlating lesion volume to permanent impedance offset;

FIG. 9a illustrates a graph showing conformance of an actual impedance curve with a predetermined desired impedance curve;

FIG. 9b illustrates a graph correlating lesion depth to percent change in impedance during ablation;

FIG. 9c illustrates a graph correlating lesion volume to percent change in impedance during ablation;

FIG. 10a illustrates a graph comparing the percent change in capacitance and the percent change in impedance to energy delivered;

FIG. 10b illustrates a graph comparing the percent change in capacitance and the percent change in impedance as a function of lesion volume;

FIG. 11a illustrates the electrode-tissue interface for determining the capacitance of healthy tissue sensed by the tip electrode of a catheter prior to an ablation procedure or during an inspection or investigation of the characteristics of the tissue (of an inorganic material);

FIG. 11b illustrates the effect of damaged tissue on the electrode-tissue interface resulting in a change in capacitance sensed by the tip electrode of a catheter;

FIG. 12 illustrates a signature of a micro-explosion in tissue on the impedance signal;

FIG. 13 is a block diagram showing integration of an industrial RF welding system with the present invention; and FIG. 14 illustrates a block diagram showing apparatus for inspecting and analyzing the characteristics of either an organic or an inorganic material.

DETAILED DESCRIPTION OF THE PREFERRED EMBODIMENT

The present invention is directed to apparatus and methodology for measuring electrical properties of organic and inorganic materials in medical and industrial applications. While the focus of the detailed detailed description of the preferred embodiment is on RF ablation of tissue, it is to be understood that the present invention can be used to monitor either organic or inorganic materials for other purposes, such as cryoablation, spinal pain management, or RF welding.

Figure 1:
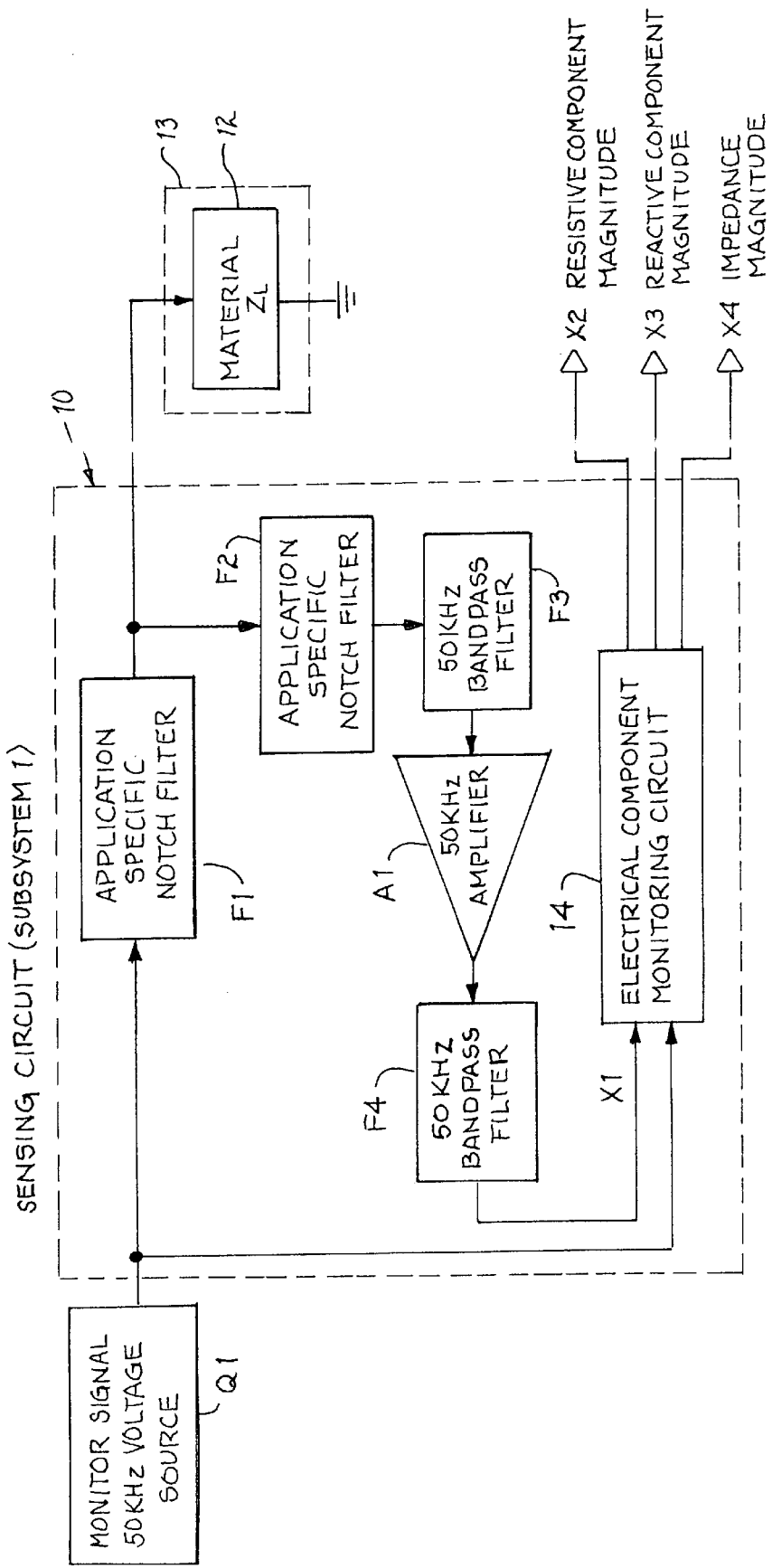
FIG. 1 illustrates a block diagram of a sensing circuit, subsystem 1.

A block diagram illustrating a sensing circuit 10 (subsystem 1) for monitoring the electrical properties of an organic or inorganic material 12 is shown in FIG. 1. A 50 KHz voltage source Q1 provides a monitoring signal to material 12 of interest through an application specific notch filter F1. Block 13 represents the apparatus necessary to apply a signal/radiation to the material. Filter F1 provides high impedance to the electrical energy used to energize the material. As an example, when integrating this sensing circuit with a computer-controlled 500 KHz RF generator 16 (shown in FIG. 4) (available from Engineering Research & Associates, Inc., Tucson, Ariz.) for performing RF ablation notch filter F1 would be a 500 KHz notch filter. The signal at node N1 is filtered through another application specific (such as 500 KHz) notch filter F2 and is further filtered through a 50 KHz bandpass filter F3, amplified by amplifier A1 and filtered by bandpass filter F4. The output signal of bandpass filter F4, X1, is also an input signal to monitoring circuit 14. Another input to the monitoring circuit is a monitoring signal provided by 50 KHz voltage source Q1.

Figure 2:
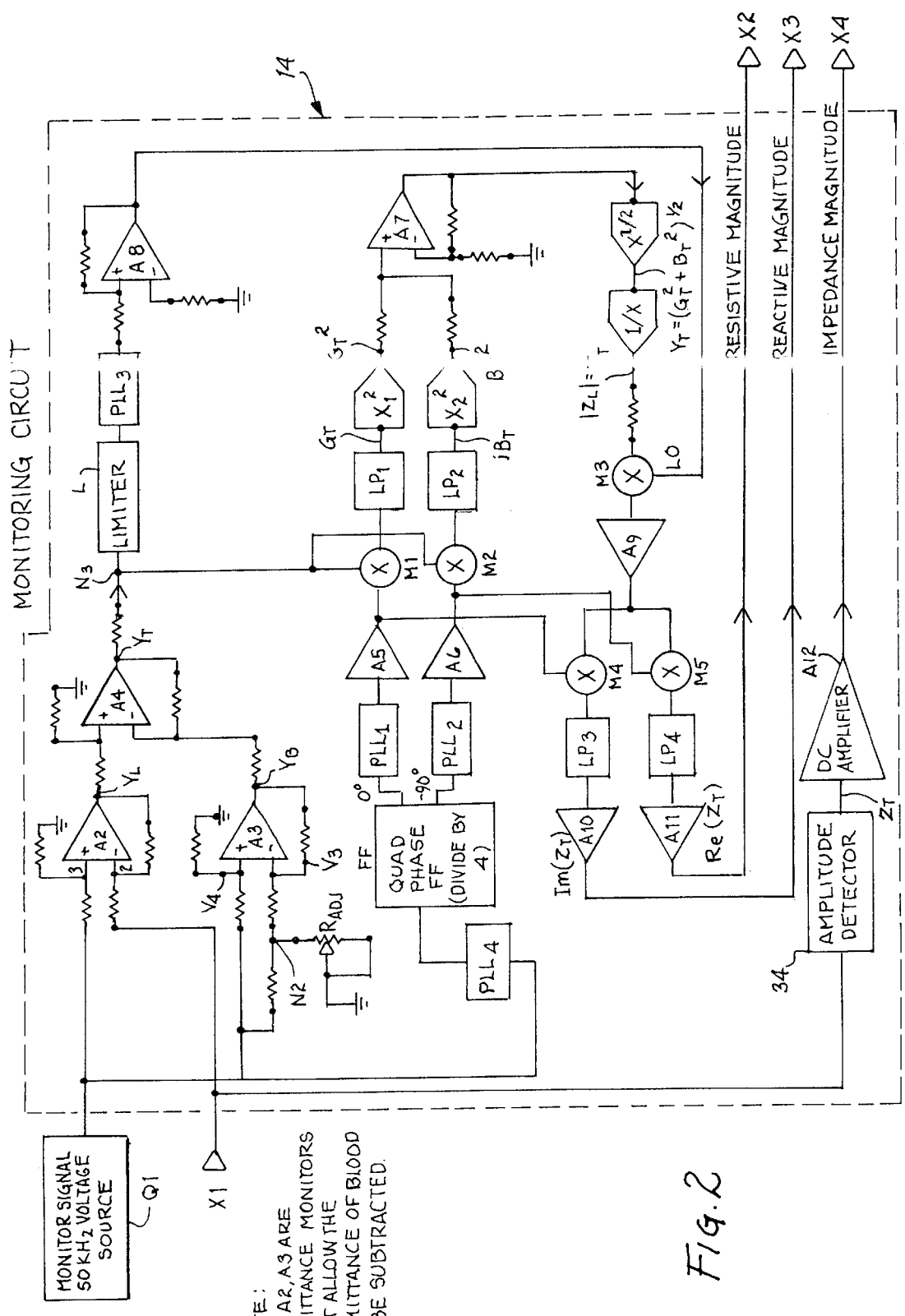
FIG. 2 illustrates a block diagram of a monitoring circuit for deriving monitor signals reflective of the magnitude of the impedance, the magnitude of its reactive component, and magnitude of its resistive component.
Figure 3:
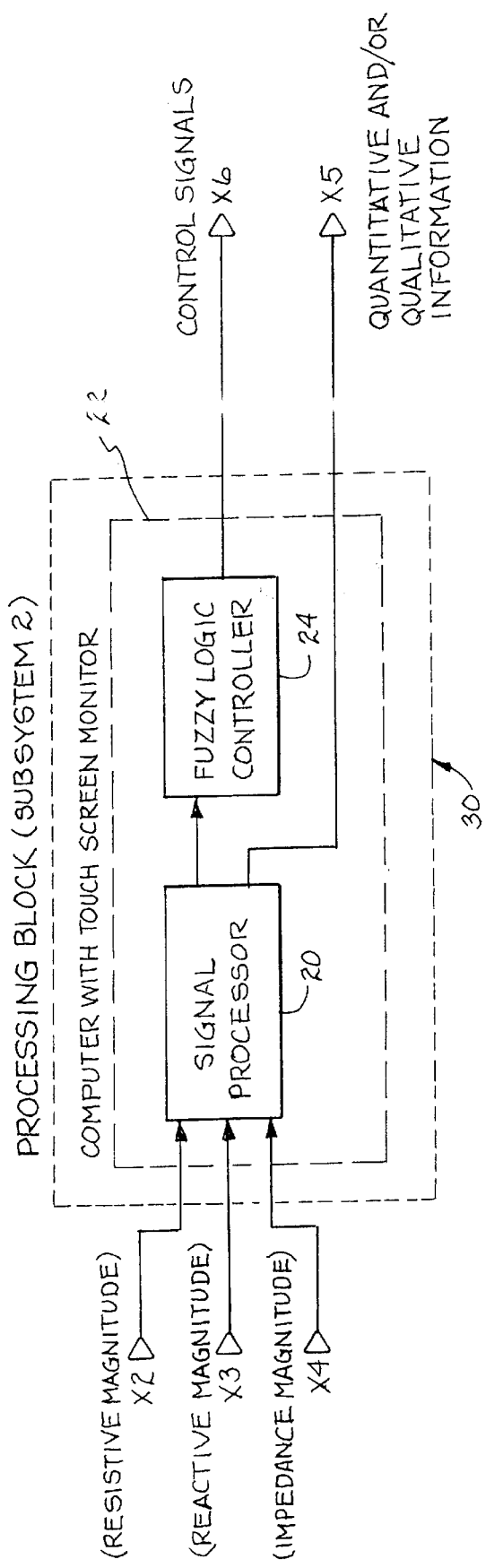
FIG. 3 illustrates a block diagram of a processing circuit, subsystem 2, for developing a control signal and other information bearing signals.
Figure 4:
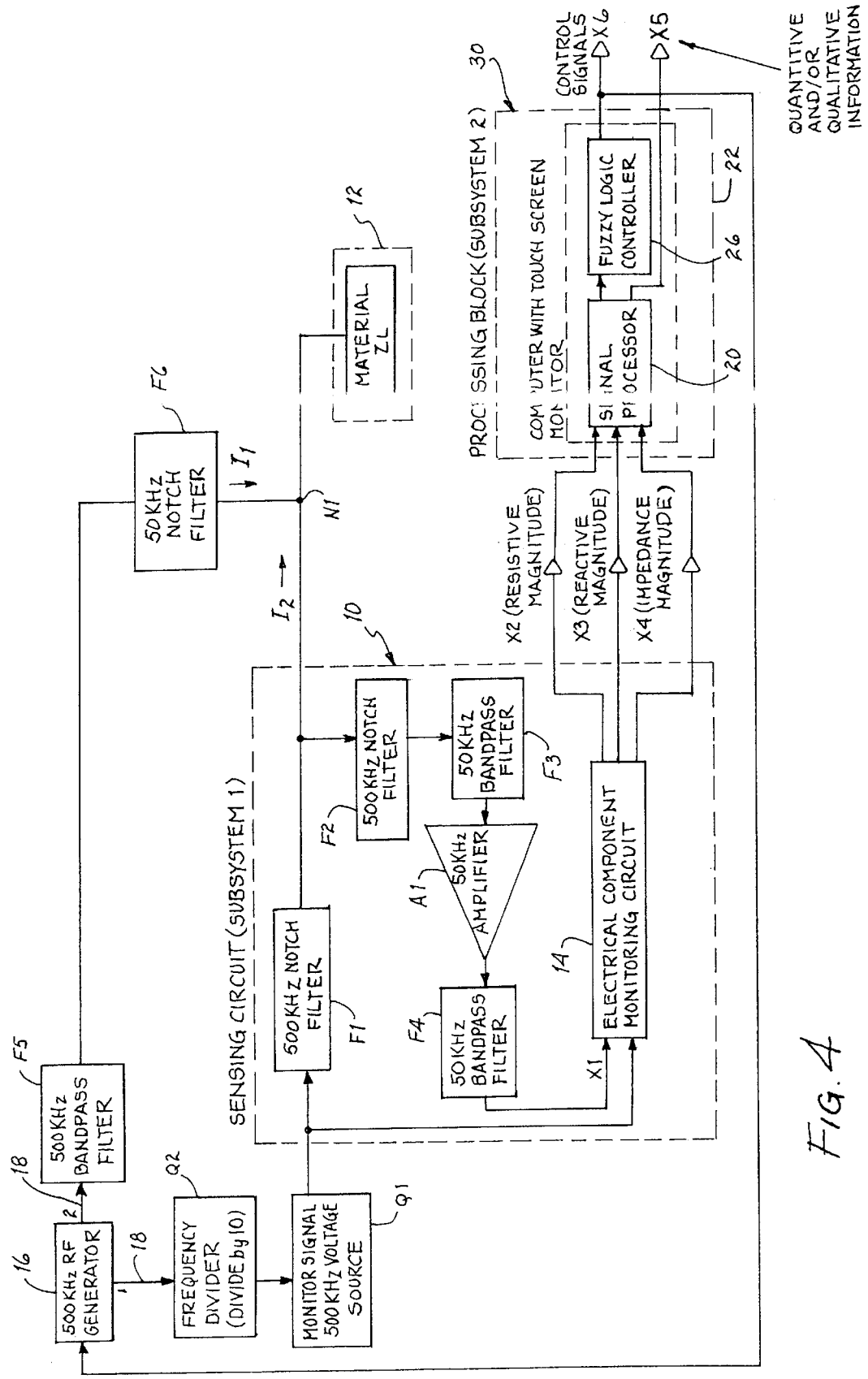
FIG. 4 illustrates a block diagram integrating subsystems 1 and 2 with a computer-controlled RF generator.

FIG. 2 shows the details of monitoring circuit 14 while FIG. 3 shows subsystem 2 for processing the output signals, X2, X3, and X4 from the monitoring circuit. FIG. 4 shows the integration of subsystems 1 and 2 with a computer-controlled 500 KHz RF generator 16.

In order to illustrate the application of the invention, a complete description of integrating the invention with an RF generator for ablating tissue (such as organic material 12) will be provided. The total system is shown in FIG. 4 including subsystems 1 and 2. Because of the complexity of monitoring circuit 14, some background information and a detailed description of its circuitry will be provided separately in the following paragraphs.

Referring jointly to FIGS. 1, 3 and 4, RF generator 16 generates a 500 KHz signal (ablation signal) having a variable amplitude, for example in the range of 0–100 Vrms at terminal 2. This signal is transmitted through buss 18 to 500 KHz bandpass filter F5 to provide the ablation signal with low harmonic distortion. The ablation signal is further passed through 50 KHz notch filter F6 and delivered to organic material 12 having an impedance load $Z_L$, which corresponds to the tissue undergoing ablation. Note that node N1 corresponds to the catheter tip electrode 42; see FIG. 5. Thus, the electrical properties are measured between the catheter tip electrode and the return ground plate 52 (or back pad); see FIG. 5. Although the electrical properties are measured between the catheter tip electrode and the ground plate in this application, they can also be measured between the catheter tip electrode and one or more ring electrodes that may be present on the catheter. It may be noted that filter F6 is a notch filter that offers a high impedance to a 50 KHz signal, which is the frequency of the monitor signal used to monitor the electrical properties of a load, such as an organic material 12.

A 500 KHz signal is also sampled at terminal 1 of RF generator 16 and is transmitted through buss 18 to a divide-by-10 frequency divider Q2. The resulting 50 KHz signal is synchronous with the 500 KHz ablation signal transmitted to load $Z_L$, which leads to improved filtering of 500 KHz harmonic noise. At node N1 there are two current flows to load $Z_L$, the ablation signal I1, and the monitor signal, I2. The sources of these two currents are isolated from each other by notch filters F6 and F1. Ablation signal I1 delivers RF energy from the catheter tip electrode to the load and heats the tissue to perform ablation at the selected ablation site as a function of the placement of the catheter. Monitor signal I2 is a low level signal transmitted to the load and produces a low level voltage at node N1. The monitor signal is passed through filter F2 and through 500 KHz bandpass filter F3. The function of bandpass filter F3 is to remove noise, which noise may be created by various sources in a practical power circuit. Amplifier A1 boosts the amplitude of the monitor signal to a value above the background noise. The monitor signal is again filtered through 50 KHz bandpass filter F4. Output signal X1 from bandpass filter F4 is directed to monitoring circuit 14. Output signals X2, X3 and X4 of the monitoring circuit are fed to a signal processor 20 of a processing block 30. The signal processor produces two output signals X5, X6. Output signal X5, the quantitative and/or qualitative signal, is displayed on an output device such as a monitor or video screen of a computer and output signal X6 (control signals) is sent to a fuzzy logic controller 26 for manipulation. Note that both the signal processor and the fuzzy logic controller are implemented by a computer 22 with a touch screen monitor (that is, the signal processor and the fuzzy logic controller may be programs executed by the computer). The output signal X6 of fuzzy logic controller 26 is fed back to generator 16 for several purposes, one of which is to control the delivery of RF energy (ablation signal).

To aid in understanding the function and operation of monitoring circuit 14, the mathematics attendant to the signal processing will be described. The input signal X1 to the monitoring circuit consists of a sinusoidal admittance signal(s) representing the sum of admittance of tissue, $Y_T = |Y_T|e^{(j\omega o + \theta T)}$ and the blood admittance, $Y_B = |Y_B|e^{(j\omega o + \theta b)}$. This signal(s) representing the admittance seen by the catheter tip electrode that is in contact with a tissue substrate imbedded in blood, which may be defined as $Y_L = |Y_L|e^{(j\omega o + \theta L)}$. To cancel the effect of the blood, a new signal, defined as, $Y_{ADJ} = |Y_{ADJ}|e^{(j\omega o + \theta B)} = 1/R_{ADJ}$, is generated. This signal is subtracted from $Y_L$. The resulting signal can now be quadrature detected to produce DC level voltages representing the admittance, $Y_T$ in rectangular coordinates, $Y_T = G_T + jB_T$. These DC signals are converted back to polar coordinates in accordance with the protocol: $|Y_T|e^{j\theta T} = (G^2_{T+}B^2_T)^{1/2}e^{j\theta T}$. The circuit next produces a signal representing the tissue impedance $Z_T$. This can be done by taking the reciprocal of $|Y_T|$ and changing the sign of its angle. To change the angle of $Y_T$, the signal is converted to RF with the necessary phase information. This can be accomplished by inputting the DC signal level to an amplitude modulator having a carrier frequency with the appropriate phase shift. The resulting sinusoidal signal represents $|Z_L|e^{(j\omega o + \theta T)}$ and is quadrature demodulated to produce DC components $Z_L = Re(|Z_L|) + jIm(|Z_L|)$, which are two (X2, X3) of the three output signals.

The circuit that performs the above described functions is shown in FIG. 2. The 50 KHz monitor signal applied to one of monitoring circuit 14 inputs is from voltage source Q1. The other input signal, output signal X1 from bandpass filter F4 (see FIG. 1), to the monitoring circuit carries information on the electrical properties of the load $Z_L$, and presented to pin 2 of amplifier A2. The 50 KHz monitor signal from voltage source Q1 is presented to pin 3 of amplifier A2. The 50 KHz monitor signal from voltage source Q1 is also presented to phase lock loop oscillator PLL4 where it is phase delayed and reduced in amplitude. The output of amplifier A2 represents admittance $Y_L$ of the load. Amplifier A3 receives a signal V3 originating from node N2, and a signal V4 from 50 KHz voltage source Q1. Signals V3 and V4 are in phase. The amplitude of signal V3 is adjusted by resistor $R_{ADJ}$ so that the output $Y_B$ of the amplifier A3 represents the admittance of blood. The admittance of blood $Y_B$ is subtracted from the admittance $Y_L$ of the load, the output of amplifier A2, by amplifier A4. The output of amplifier A4 represents the summed admittance $Y_T$ present at node N3.

Phase lock loop oscillator PLL4 has a 200 KHz output phase locked to the 50 KHz monitor signal. Quadraphase flip-flops FF divides its input frequency by four (4) and produces two output signals at 50 KHz phase shifted by 90 degrees. These output signals are digital pulses that require filtering without significant phase delay. Phase lock loop circuits PLL1 and PLL2 accomplish this filtering. The respective signals are amplified by amplifiers A5 and A6 to become the injection signals for multipliers M1, M2, M4, and M5. Multipliers M1 and M2 provide DC output level signals along with many harmonics of the introduced 50 KHz signal. The DC components of these signals are extracted by low pass filters $LP_1$ and $LP_2$, respectively.

These filtered signals represent $G_T$ and $jB_T$ and are squared by blocks $X_1^2$ and $X_2^2$. Summing amplifier A7 performs summing of these signals. Block $X^{1/2}$ performs a square root operation to produce $|Y_T|=(G_T^2+B_T^2)^{1/2}$. The operation of $|Z_T|=1/|Y_T|$ is performed by block 1/X. The resulting DC signal is converted to an AC signal of correct phase by multiplier M3. The injection signal for multiplier M3 is derived from node N3 via amplitude limiter L, phase lock loop PLL3, and amplifier A8. The output of multiplier M3 represents $|Z_T|e^{(j\omega r-\theta T)}$ and is amplified by amplifier A9. The output of amplifier A9 is quadrature demodulated by multipliers M4 and M5. It may be noted that the injection signals for these multipliers are derived from amplifiers A5 and A6, respectfully, which signals have a 90 degree phase difference. The output signals of multipliers M4 and M5 are filtered by low pass filters LP3 and LP4 and the filtered signals are amplified by amplifiers A10 and A11, respectively. The voltage outputs of amplifiers A10 and A11 represent the signals $Re(Z_T)$ and $Im(Z_T)$, respectively. Signal $Im(Z_T)$ represents the reactance component of total impedance $Z_T$ while $Re(Z_T)$ represents its resistance component and are identified as X3 and X2, respectively. The actual capacitance of the tissue in contact with the catheter tip electrode is defined as $C=1/2\pi 50e3Im(Z_T)$. The calculation of capacitance C in accordance with this equation is readily done by computer software present within computer 22 (see FIGS. 4 and 5). Signal X1 inputted to the monitoring circuit 14 is also conveyed to amplitude detector 34. DC amplifier A12 receives the output of amplitude detector 34 and by the calibration and amplification factor of the detector, produces a voltage output representing the impedance magnitude $Z_T$, signal X4. It is to be understood that the above described functions can be performed by hardware or software (using digital signal processing (DSP) techniques, for example).

The above paragraph describes in detail the apparatus and method of subsystem 1 (FIG. 1) of the present invention, which provides accurate measurements of the magnitude of the resistive component, the magnitude of the reactive component, and the magnitude of the impedance of an organic or inorganic material.

FIG. 3 illustrates subsystem 2 of the present invention. Subsystem 2 includes a processing block 30 incorporating a signal processor 22 and a fuzzy logic (FL) controller 24 which are a part of computer 22 and its touch screen monitor.

The main function of subsystem 2 is to process input signals X2, X3 and X4 received from subsystem 1, and to provide control signals (X6) as well as qualitative and quantitative information in the form of specific signals (X5) for acquisition, manipulation, and system control.

The motivations for using an FL controller, instead of a classical PID controller or other controller(s), are the following. First, an FL controller allows multiple input signals to be implemented easily whereas a classical controller only allows one specific input signal. Second, unlike a classical controller, a FL controller is designed, through mathematical manipulation of the data set, to handle signals that are not precise. Third, a FL controller utilizes expert opinions when deriving an output, an important feature not found in the classical controllers. The ultimate aim and purpose of the FL controller used herein is to generate control signals that will result in delivery of RF energy to the organic or inorganic material in a manner consistent with controlling a parameter to achieve a specified result.

All biological membranes share a common and fundamental structural plan. A biological membrane of a cell is a plasma membrane made primarily of a thin double-sheet (a "bilayer") of fatty lipid molecules that cover the surface of the cell forming a barrier to the movement of many molecules including charged ions. This impermeant bilayer effectively separates an electrical charge across the membrane and can be modeled accurately as a capacitor; the resulting capacitance gives rise to the reactive component of the impedance of the tissue. The membrane capacitance, or reactance, is directly proportional to the surface area of the cell and relies on the integrity of the membrane structure. The capacitive current (Ic) is related to the membrane capacitance (Cm) and a change in voltage (dV/dt). That is, Ic=Cm*dV/dt. Membranes from diverse species of animals show a similar membrane capacitance, which is approximately 1 microfarad per $cm^2$. If the membrane is disrupted physically, the ability to separate an electrical charge is lost, and will result in a reduction or loss of the capacitive characteristic. During RF ablation, frictional heat is believed to cause physical damage to the tissue. The physical damage to the tissue, which could also result from irradiating the tissue, freezing the tissue, subjecting the tissue to ultrasound energy, etc., is expected to cause a change in the tissue capacitance that reflects the degree of damage to the cell membranes.

Also present within the membrane bilayer are a number of protein molecules that form pathways for selected movements of salts, nutrients, and signals. Those protein pathways that are specialized for mediating ion fluxes (known as "ion channels") enable regulated net charge movements across the membrane. These ionic currents are the essential forces that drive changes in voltage, constituting the electrical activity in brain, heart, and muscle cells that lead to functional outcomes (such as contraction of the heart). These ion channel proteins are accurately modeled as variable resistors in the electronic model of the membrane and their influence on the voltage signal is described by Ohms Law, Vm=Rm*Im, where Vm is membrane potential, Im is the flow of current across the membrane and Rm is the resistance of the membrane. The resistance of the membrane is inversely proportional to the number of open channels (conductance) and the selective gating of ion channels requires integrity of the membrane. With disruption of the membrane leading to denaturation of the proteins and the membrane structure, Rm should decrease as unregulated leak pathways are created in the damaged tissue.

Figure 5:
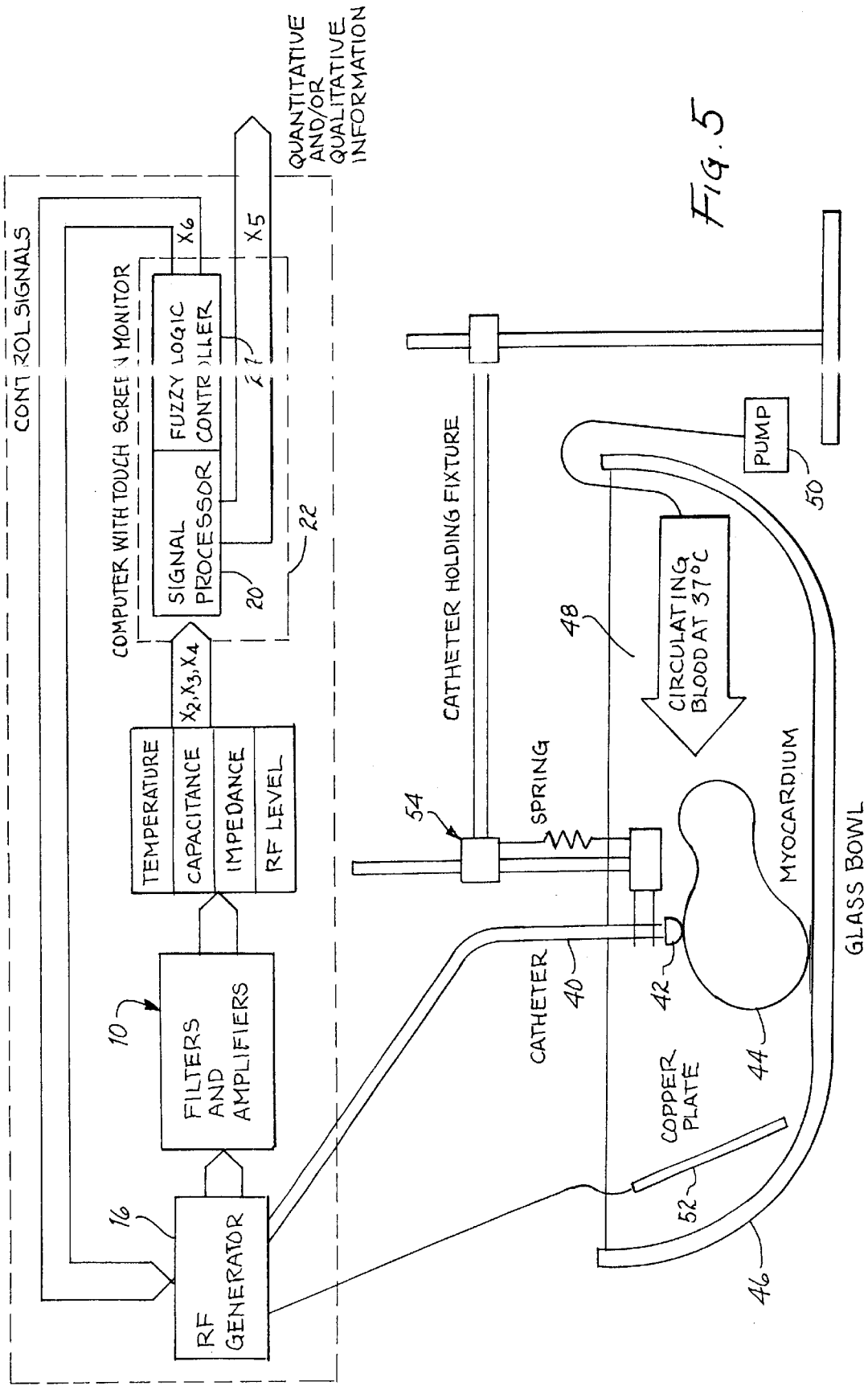
FIG. 5 illustrates apparatus used for testing and confirming operation of the present invention.

All of the results obtained below, except for those obtained from a third party in privity with the present assignee, were conducted using the apparatus shown in FIG. 5. The in vitro experiments were performed with 7-French cardiac ablation catheters 40. These catheters have a thermocouple mounted in a 4 mm distal electrode 42. RF power was delivered with a computer-controlled RF generator 16 (Engineering Research & Associates, Inc., Tucson, Ariz.). Fresh bovine ventricular myocardium 44 was immersed in a temperature-controlled bowl 46 having circulating heparinized, fresh bovine blood 48 at 37° C. recirculated by a pump 50 at a flow rate of 1 liter/minute. A copper return plate 52 was immersed in the blood; the plate could also be placed adjacent to or in contact with the myocardium. Distal electrode 42 was oriented perpendicular to the epicardial or endocardial surface of the myocardium, as shown. On-line real-time data of RF energy, thermocouple-tissue interface temperature, tissue reactive component, tissue resistive component, and tissue impedance were displayed simultaneously on the screen of computer 22 and recorded for analysis. As mentioned earlier, the electrical properties were measured between the electrode 42 and the return plate 52.

Recent validations of the present invention's capability for the sensitive measurement of the resistive component, reactive component, and impedance signals were demonstrated both in-house and by a third party in privity with the assignee. FIGS. 6a–7b illustrate data collected from in vitro experiments with the computer-controlled RF generator 16 and the embodiment shown in FIG. 4, performed by third party researchers in privity with the assignee; only these results were presented at NASPE $22^{nd}$ Annual Scientific Sessions without disclosing the nature of the invention itself (Matsudaira et. al., "Highly sensitive impedance monitoring may predict electrode contact pressure and lesion size during radiofrequency ablation using a saline irrigated catheter", (poster) NASPE May 2001). The average initial impedance (FIG. 6a), obtained prior to the delivery of energy for 0 g of contact weight was 100±4Ω, for 5 g of contact weight was 126±11Ω, and for 20 g of contact weight was 170±19Ω. These data were collected with an apparatus similar to that shown in FIG. 5. The different contact weights were obtained by varying a spring-loaded device similar to spring support device 54 shown in FIG. 5. Comparing these data obtained with the present invention to the data obtained from prior art RF generators (which provide approximate initial impedance of 113±16Ω for poor contact of an estimated 5 g contact weight and 139±24Ω for good contact of an estimated 20 g contact weight; not shown), the present invention provides measurements with substantially greater resolution and sensitivity. As indicated earlier, the difference in the average initial impedance between good and poor contact for catheter placement on tissue, as assessed by prior art generators is 26Ω (139Ω–113Ω), whereas the average difference in the initial impedance obtained by the present invention is 44Ω (170Ω–126Ω). This 44Ω difference was obtained under the conditions of 5 g contact weight representing poor contact and 20 g contact weight representing good contact. Clearly, even under this condition of allowing 5 g contact weight to represent poor contact and only 15 g of contact weight distinguishing poor contact from good contact, the present invention provides, on average, an impedance measurement with approximately twice the sensitivity and resolution of the prior art generators. If one uses 0 g contact weight to represent poor contact and 20 g contact weight to represent good contact, the average difference in the initial impedance provided by the present invention is 70Ω (170Ω–100Ω), which is approximately 3 times (139Ω–113Ω=26Ω) the resolution and sensitivity provided by prior art generators. Furthermore, the standard error of the impedance measurements provided by the present invention is smaller than the error provided by prior art generators, which indicates that more precise measurements are obtained by the present invention.

With such sensitivity, it is possible to not only qualify (no, poor, fair, or good) contact quality but also quantify it. There are many ways to qualify and quantify contact quality from impedance measurements. Three methods were used in the present invention. The first method involved the use of fuzzy logic, which is particularly well suited because of the nature of the signals. The second method utilizes a well-known statistical based approach called maximum likelihood method used together with multiple interacting models. The third method is a direct one to one conversion from the impedance signal to contact quality. As a simple illustration of the third method, FIG. 6a shows that 80% of the impedance measurements fall between 97 and 104 for 0 g of contact weight, between 116 and 141 for 5 g of contact weight, and between 150 and 196 for 20 g of contact weight. Observe also that the $10^{th}$ to $90^{th}$ percentile ranges for each of the contact weights do not overlap one another. Therefore, if quantization of the continuous contact weight to discrete levels is acceptable, the lack of overlap can be used to differentiate between different contact weights. In addition to the three stated methods, a curve fitting approach, such as least square error fitting, can be used. Regardless of the methods used, it suffices to mention that the focus of the present invention is the utilization of the sensitive impedance signal for qualifying and quantifying contact quality.

It is also important to observe that, unlike the prior art generators, the present invention can measure the impedance signal in real time prior to the delivery of energy. Further, the present invention continues to generate output signals in real time during and after the delivery of energy. Hence, with the present invention there is no need to determine the contact quality through observation of the change in tissue impedance or electrode temperature during ablation, which serves to eliminate the previously required time associated with such determinations (recall that prior art generators require energy to be delivered before any tissue impedance can be measured).

FIG. 6b shows the percent change in impedance during ablation. FIG. 6b shows that for 0 g of contact weight the percent change in impedance during ablation is less than 10%. The percent change in impedance ranges from 12 to 22% ($10^{th}$ to $90^{th}$ percentile) for 5 g contact weight and from 27 to 44% for 20 g contact weight. Percent change in impedance is defined as the relative difference in impedance at the onset of energy delivery (start of ablation), which is the initial impedance, and at the termination of energy delivery (end of ablation), which is the final impedance (that is, percent change in impedance equals $(Z_i-Z_f)/Z_i$, where $Z_i$ is the initial impedance and $Z_f$ is the final impedance). It is evident from the data that the percent change in impedance during ablation provides an indication of the contact weight. Although FIG. 6b shows an interesting relationship between percent change in impedance during ablation and contact weight, it is more important to estimate the lesion size or formation at the termination of the ablation energy. This makes sense since it is somewhat pointless to quantify contact weight after an ablation procedure.

FIGS. 7a and 7b show the trend of increasing ablation depth correlating with both the increase in percent change in impedance during ablation and with higher initial impedance. FIG. 7a suggests that the lesion depth is linearly correlated to the initial impedance with a correlation factor (r) of 0.73; correlation factors can range between −1 and 1.

A negative correlation factor indicates that the data are inversely related while a positive correlation factor indicates that the data are directly related. The larger the magnitude of the correlation factor, the better the correlation. FIG. 7b shows a similar linear relationship between lesion depth and percent change in impedance during ablation except that it has a higher correlation coefficient (r value) of 0.77. As is evident from the data, the resolution possible from the present invention for the measurement of impedance allows the lesion depth to be approximated from either the initial impedance measurement or from the percent change in impedance (note that the absolute change in impedance can also be used). One simple way of obtaining the lesion depth from the impedance signal is through curve fitting. There are many curve fitting methods with the least square error approach being the most popular. Once the equation for the curve with the depth as the dependent variable and the impedance as the independent variable is found, the lesion depth can easily be estimated with the measured impedance (or change in impedance).

Another measurement that can be used to estimate lesion volume and depth is the permanent change in the tissue impedance. Permanent change in tissue impedance is defined to be the difference between the initial tissue impedance (at the onset of ablation) and the tissue impedance after it has cooled down to body temperature (after ablation). FIG. 8a shows the definition of permanent tissue impedance change while FIGS. 8b and 8c show the correlation between permanent tissue impedance change and the corresponding volume and depth of the lesion that was created by RF ablation. Referring to FIG. 8a, the onset of energy delivery occurs at approximately 22 seconds. During the ablation process, the impedance signal decreases until energy delivery is terminated at about 85 seconds. As soon as the energy delivery is terminated, the impedance signal starts to increase. This phenomenon is associated with the cooling process of the tissue and, as will be discussed in a later section, is mostly associated with the resistive component of the tissue, which is a signal provided by the present invention. However, the impedance signal does not completely recover to the initial amplitude. This loss in impedance is referred to as permanent impedance change and is associated with the altered properties of the tissue due to the damage inflicted upon it. If the tissue does not sustain any permanent damage during ablation, the results show no permanent change in the impedance, as the impedance of the tissue after it has cooled is found to return to its initial value. It must be emphasized that, even though in case the tissue does not sustain any damage, the overall impedance signal amplitude will decrease during ablation because of thermal effects (an interesting occurrence that can be used to estimate tissue temperature, as will be discussed later). Since the permanent change in impedance is caused by the altered properties of the damaged tissue, this change is expected (and found to) to correlate to lesion size.

Comparing FIG. 8b to FIGS. 7a and 7b, it is evident that the graph shown in FIG. 8b demonstrates a trend similar to those found in FIGS. 7a and 7b. That is, lesion depth seems to be linearly correlated to the permanent change in impedance with a correlation factor (r) of 0.76. FIG. 8c also shows a similar relationship between lesion volume and the permanent change in impedance. Note that the three methods used for qualifying and quantifying contact pressure based on tissue impedance measurements can be used here to quantify lesion size in a similar manner. In addition, using the curve fitting method to estimate lesion depth from the permanent change is also a viable approach.

Given the strong correlation between changes in impedance and the production of a lesion, it stands to reason that if the impedance could be controlled to follow a curve with a specific percent change, a lesion of desired size could be obtained in a controlled fashion. This concept was verified with in vitro experiments and the results are shown in FIGS. 9a, 9b and 9c. FIG. 9a shows that the impedance signal can be controlled to approximately follow a desired curve with user-specified offset in impedance as a percentage of the initial baseline value. The desired curve, shown as a dashed line in FIG. 9a, is generated from an equation with three user-specified parameters. The first parameter is the initial slope of the impedance drop, $dZ/dt$. The second parameter is the duration of the slope, $\Delta t$, and the third parameter is the percent change in the impedance, % Z. The equation with the mentioned parameters is programmed into computer 22 and used by fuzzy logic controller 24, to control the delivery of the energy in a manner consistent with guiding the measured impedance to track the desired impedance. FIGS. 9b and 9c show the correlation between lesion depth and volume and the percent change in impedance. As illustrated in FIG. 9b, the relationship between lesion depth and percent change in impedance is linear. Furthermore, note the "tightness" (low error) of the data. Eighty percent of the depth measurements fall between 2.0 and 3.5 mm for a programmed impedance offset of 10%, between 2.9 and 4.3 mm for the programmed impedance offset of 20%, and between 4.0 and 5.2 mm for the programmed offset of 30%. A more remarkable result obtained from controlling impedance is its immunity to factors that are traditionally considered uncontrollable. For example, with the same impedance control settings, lesions of consistent size can be reliably obtained over a wide range of contact quality and blood flow rate. The same cannot be said for conventional signal controls such as those incorporated into prior art generates that focus on the control of electrode temperature, RF voltage, or power. FIG. 9c demonstrates the same linear relationship between lesion volume and percent change in impedance. From these data, it is evident that lesion volume and depth can be controlled. Note that the lesion volume is calculated as $\frac{2}{3}\pi \times (0.5 \times \text{lesion depth}) \times (0.5 \times \text{lesion length}) \times \text{lesion width}$ (Mackey, et. al., "Simultaneous multipolar radiofrequency ablation in the monopolar mode increases lesion size", PACE 1996; 19(7) :1042–8).

The present invention including the impedance control technique, is particularly useful in a static environment such as is found in conditions of kidney or liver tumor ablation. This impedance control technique can also be applied to cardiac ablation. As mentioned above, an added benefit of controlling impedance is that the lesions created are quite consistent over a rather wide range of contact quality (for example, poor contact is automatically compensated for by the controller through the delivery of higher RF energy). Furthermore, unlike systems that rely on catheter thermocouple temperature as the variable for control, a system using impedance control produces more consistent lesion sizes for different catheters. Temperature control is problematic in that it may produce no lesion in one case (controlling a standard catheter at 35 degrees centigrade, for example) and may seriously injure a patient in another case (controlling a chilled catheter at 65 degrees centigrade, for example).

The better resolution and greater sensitivity in the impedance signal obtained with the present invention allows the user to monitor and quantify the quality of contact between the catheter and the tissue before ablation begins, to control lesion size during RF energy application, to confirm lesion formation and to estimate lesion volume after the RF energy application is complete. There is an undeniable need for this technology, based on its highly sensitive impedance signal for verifying all aspects of catheter electrode placement, energy delivery, and desired outcome.

The impedance signal, when dissected into its complex components, shows further information content. Specifically, the reactive component of the tissue alone, as measured by the present invention, provides another sensitive signal that correlates to lesion formation. In vitro experiments provide data (FIG. 10a) showing that the percent change in the impedance signal during ablation for the range of energy delivered was between 30% and 60%. However, the tissue capacitance, or reactance component for the same range of applied energy was altered by 160% to 400%, which clearly indicates that the reactive component of the impedance was about five times more sensitive than the impedance in detecting the extent of ablation. The graph in FIG. 10b shows similar result for the percentage change of the tissue impedance signal and the tissue reactance component signal as a function of lesion volume. This huge gain in resolution and sensitivity provided by the reactive component of the impedance signal can be immediately capitalized upon to qualify and quantify contact quality as well as provide a basis for estimating and controlling lesion formation and lesion size.

FIGS. 11a and 11b illustrate a hypothetical presentation that is consistent with the dramatic increase in tissue capacitance observed during RF energy application. As mentioned earlier, the electrical properties of the tissue are measured between the electrode of the catheter and the return plate. More particularly, the tissue capacitance is measured between catheter tip electrode 42 and the copper plate 52 (see FIG. 5). Before energy delivery, the catheter tip electrode is in contact with healthy tissue 58 whose cells 60 are intact and are not ruptured or damaged. These cells, as described above, have capacitive and resistive properties. The capacitance of the tissue seen by the catheter electrode 42 is a function of the size of the tissue-electrode interface 62 and the copper plate. Since the surface area of the tissue-electrode interface is much smaller than that of the copper plate, the capacitance seen by the electrode is dominated by the tissue-electrode interface. As the tissue 58 adjacent the catheter electrode 42 starts to rupture due to applied RF energy and heating, it loses its capacitive properties and also undergoes a reduction in resistively (i.e., the region 64 of damaged tissue transforms to a region of low resistance, See FIG. 11b). This low resistance region of tissue 58 can be viewed as an extension of the electrode, leading to a new effective electrode-tissue 66 interface illustrated as bold lines on the FIG. 11b. Since electrode-tissue interface 66 has a larger surface area than the area of initial electrode-tissue interface 62, the tissue reactive component increases.

In recent in vivo tests conducted on a canine heart by physicians in privity with the assignee and under the auspices of the assignee, the above described benefits and results of in vitro tests were confirmed, as set forth below. The average initial impedance with the catheter and blood only and no contact between the catheter tip electrode and the cardiac tissue was 134Ω. To confirm and verify the quality of the catheter tip electrode/tissue contact, an ultrasound device was used to provide real time imaging of the relationship between the catheter tip electrode and the cardiac tissue. Thereby, good, fair and poor contact could be established and maintained throughout each EP procedure on the beating heart.

For good catheter tip electrode/tissue contact (when the electrode was in firm contact with the heart tissue) the average initial impedance was 232Ω before application of the ablation signal, a difference of 98Ω (232Ω–134Ω). The average impedance at termination of the constant voltage ablation signal was 171Ω, a change of 61Ω (recall the average 20Ω drop achieved with a prior art generator). The difference in the impedance measured without contact and that measured with good contact provides nearly a 2:1 ratio, which is easily and readily discernable by a physician performing an EP procedure. The change in impedance over the course of delivery was over 25% (relative to initial impedance before energy delivery). The increased range of impedance change that can be measured with the present invention permits precise control using described methods to achieve the size of lesion sought.

For fair catheter tip electrode/tissue contact (when the electrode was in moderate contact with the heart tissue) the average initial impedance before application of the ablation signal was 195Ω, a difference of 61Ω from no contact and a difference of 37Ω from good contact, which is again an easily discernible change compared to both contact conditions. The average impedance at termination of the constant voltage ablation signal was 149Ω, producing a percent change in impedance over the course of energy delivery of over 20%.

For poor catheter tip electrode/tissue contact (when the electrode was in light contact with the heart tissue) the average initial impedance before application of the ablation signal was 153Ω, a difference of only 19Ω above no contact. The average impedance at termination of the constant voltage ablation signal was 131Ω, a change of 22Ω and less than 15%. This change in impedance is considered small using the present invention and a minimal lesion would be expected. Also, it was apparent from the impedance measured before energy delivery that poor contact had been established between catheter tip electrode and the tissue using the present invention. Similar initial impedance measurements would be considered to indicate good catheter tip electrode/tissue contact using prior art generators.

As noted earlier, one of the potentially injurious conditions that should be avoided in neural or cardiac applications is the micro-explosion phenomenon. Micro-explosions occur when an excessively high temperature is produced in the tissue and steam begins to form. As more energy is delivered to the tissue, steam accumulates within a confined region below the tissue surface (a steam pocket), increasing its pressure. The steam pocket eventually explodes resulting in a micro-explosion. The physical process of a micro-explosion is reflected electrically in transient, and in some cases permanent, alterations in the tissue's local electrical properties. The signature of micro-explosion is usually a small sharp deflection 70 in impedance signal 72, as illustrated in FIG. 12. After the micro-explosion, the impedance appears to drop back down. On some occasions instead of dropping back down after a micro-explosion, the impedance signal maintains a higher value, perhaps due to the presence of steam bubbles still trapped underneath the catheter tip electrode or due to charring of the tissue surface. The sensitive impedance measurement capability of the present invention can be used to detect the occurrence of these micro-explosions.

Despite an often noticed rise in the impedance signal, there is still a need for a signal that is unambiguous and more responsive to micro-explosions. This need exists because the signature of a micro-explosion on the impedance signal is sometimes too small to be identified. The measured reactance signal provided by the present invention can be used for this purpose since at the onset of steam formation the tissue reactance decreases and then increases dramatically due to a larger electrode-tissue interface following the micro explosion(s). As the reactance component changes more dramatically than the impedance because of the resulting real time change in capacitance, micro-explosions are expected to be detected more clearly and consistently by the reactive signal (X3).

Preventing overheating in the tissue is of foremost importance in an EP procedure. Extreme tissue temperatures can lead to various injurious conditions, including micro-explosions. It has been observed from experiments that tissue reactance, unlike impedance, does not change significantly with temperature. This implies that during an ablation the resistive component of the tissue impedance is responsible for most of the thermal changes in the impedance signal. Therefore, it makes sense to use a measurement of the resistive component (X2) provided by the present invention to estimate tissue temperature. It is assumed that a tissue resistance can be modeled according to $R=R_0[1+\alpha(T-T_0)]$ where R is the instantaneous resistance of the tissue, $R_0$ is the resistance at temperature $T_0$, T is the instantaneous temperature, and $\alpha$ is the temperature coefficient of resistivity. (D. Halliday, R. Resnick, "Fundamentals of Physics", $3^{rd}$. Ed., 1988). There are at least 3 ways to estimate tissue temperature using the signals measured and provided by the present invention. First, the resistive component signal (X2) can be used either to create a statistical model of the tissue temperature or to correlate the resistive component with the tissue temperature. Second, information can be extracted from the resistive component and used in conjunction with the electrode temperature, or other suitable signals provided by the present invention, to solve a standard differential thermal equation. Third, the equation described above can be used to solve for T iteratively where $R_0$ equals the initial resistive magnitude prior to ablation, $T_0$ is the initial tissue temperature, and R is the measured instantaneous resistance provided by the present invention. The parameter $\alpha$ can be experimentally determined.

There is another approach to estimate tissue temperature provided by the invention. Since tissue reactance is not observed to be significantly affected by temperature and since it is indicative of tissue damage, it can be used to estimate the permanent change in tissue resistance caused by tissue damage beyond the changes in electrical properties due to temperature alone. The equation that translates the capacitance change to permanent resistance change can be experimentally derived. This estimated permanent change in tissue resistance could in turn be used in conjunction with the measured resistive component, or other signals to obtain a new signal that is strictly a function of temperature alone. (Note that the methods described in the previous paragraph do not account for the permanent change in tissue resistance. Those methods simply assume that the permanent resistance change is insignificant when compared to the transient thermal change.) This new signal can then be used in a similar manner as described in the previous paragraph to estimate tissue temperature, which can in turn be used for control purposes.

Since tissues of different textures have different electrical properties, the sensitive measurements provided by the present invention can be used to differentiate between them. Also, since the electrical properties are different for healthy tissue, tumor, and infarct tissue, the invention can also be used to differentiate between them by using apparatus shown in FIG. 4 without energizing the ablation signal.

While the above invention has been thoroughly described in detail with reference to RF ablation, it should be clear and obvious that the present invention can be applied to ultrasound ablation, cryogenic ablation, spine pain management, and other therapeutic procedures.

While the above description of the invention seems to segregate hardware from software, it should be clear and obvious that any portion of the hardware can be implemented in software (through DSP for example) and inversely, any portion of the software can be implemented with hardware.

The present invention can be applied to industrial applications in a manner similar to those described for medical applications. For example, in RF welding, the real-time measurements provided by the present invention can be used to prevent arcing, (which if undetected can cause substantial damage to the welding system), by detecting the existence of an air gap, inclusions in the material, missing material, imperfect or defective material, etc. Further, as in tissue temperature estimation and control, the same approach can be used to estimate and control an inorganic material's temperature in order to control heating and energy delivery to avoid over-heating. The present invention can also be used to identify the changes in a material's electrical properties due to aging or storage condition. Furthermore, the measurements provided by the present invention can be used to manually or automatically adjust matching circuitry for optimal matching, to determine if a weld has occurred, and if so, the resulting quality of the weld.

A detailed example employing the teachings of the present invention using inorganic materials follows. The circuit shown in FIG. 13 may be used to control the impedance of a load by modulating the pressure and displacement of plastics during a welding process. The prior art technology utilizes high pressure and high power to brute force a weld. Use of power in the range of 2 kilowatts to 50 kilowatts is common practice. The plastic's compression, melting and displacement phases occur simultaneously using the brute force approach and a matched impedance is presented to the power generator for a brief period of the welding cycle. Consequently, the welding system operates at an energy delivery efficiency on the order of 10 to 20%. This efficiency is improved to 70 to 80% by real time monitoring of the load impedance and adjusting the pressure of the electrodes across the plastic for a static impedance match until the plastic has reached a desired temperature, after which the plastic is compressed and displaced and the weld cycle is terminated. The plastic temperature can be characterized by monitoring the ratio of its resistive and reactive components of impedance.

FIG. 13 illustrates an example of an application of the present invention to an industrial RF welding system. Comparing FIG. 13 to FIG. 4, it is clear that only slight modifications are needed. For purposes of clarity and consistency common reference numerals will be used for common elements performing essentially common functions. First, the application specific notch filters, F1 and F2, are now 40.68 MHz notch filters, instead of 500 KHz notch filters, since generator 16 now utilizes a 40.68 MHz frequency. Also, filter F6 is now a 200 KHz notch filter, instead of a 50 KHz notch filter, since the monitoring signal used has a frequency of 200 KHz. Similarly, filters F3 and F4 and amplifier A1 have been changed from 50 KHz to 200 KHz. These changes are apparent to and easily made by those skilled in the art. Depending on the application, the components' value in the electrical component monitoring circuit 14 may also need to be modified to account for the frequency change of the monitor signal. The two plastics to be welded are represented as plastic material A and plastic material B, respectively. In this example, the two plastics are held together by two electrodes, namely live electrode 80 and the ground electrode 82, at a site on the plastics to be welded. The force needed to keep the two electrodes clamped can be obtained from a pair of clamps 84, 85, whether by manual, electric, or hydraulic power, shown representatively in FIG. 13. A control signal (X6) may be applied to an actuator of clamp 84 to control its operation; it is assumed that clamp 86 serves in the manner of a non moving pedestal or table. Note that the weld need not be limited to a single spot weld but can be of various shapes and sizes. Comparing FIG. 13 with FIG. 4, it is clear that material (tissue) 12 shown in FIG. 4 is simply replaced by plastics A and B shown in FIG. 13. The rest of the components are interconnected in the same way as described with reference to FIG. 4. However, there are two primary differences between the apparatus shown in FIGS. 4 and 13. First, unlike FIG. 4, source Q1 for the monitor signal is not derived from generator 16 and is provided by monitor signal source Q1. However, it can be derived from generator 16 to obtain improved filtering, if necessary. Thus, FIG. 13 illustrates a variant that may be possible without departing from the scope of the present invention. The second difference is the inclusion of matching circuitry 90. As mentioned earlier, the electrical properties measurements obtained with the invention can be used to optimize the electrical match of the load to the system to improve energy efficiency and to protect the system from damage. The control signal output of the fuzzy logic controller 24 is directed to generator 16. These control signals can be used to control the generator in various ways, one of which is to control the delivery of the RF energy.

FIG. 14 illustrates apparatus for analyzing the characteristics of an organic or inorganic material 100. The circuitry and signal processing apparatus illustrated and described with respect to FIG. 13 is duplicated in FIG. 14 expect for the apparatus and circuitry relating to generation and application of an ablating/welding signal (radiation). In particular, generator 16 bandpass filter F5, notch filter F6, and matching circuit 90 shown in FIG. 13 have been omitted along with the feedback of control signal X6 to the generator 16. Thus, the apparatus and circuitry illustrated in FIG. 14 applies a monitor signal to material 100. An output signal X1 is developed to reflect any real time change to the monitor signal. The monitor signal (from source Q1) is correlated with the output signal (X1) to determine the magnitude of the impedance of the material and the magnitudes of the resistive (X2) and reactive (X3) components of the impedance and signals X4, X2 and X3, respectively, are produced. Signals X2, X3 and X4, are processed in processing block 30 to provide control signals (X6) and information signals (X5) along with display of indicia indicative on a real time basis of the characteristics of the material.

To determine the presence of different characteristics of the material as a function of location on the material, electrode 80 may be laterally moveable, as representatively depicted by arrows 102, 104. Alternatively, if electrode 82 serves in the manner of a pedestal to support material 100, it may be moved laterally (or otherwise) relative to electrode 80 to permit electrode 80 to inspect different locations of the material.

While the above discussion is oriented toward inspecting an organic or inorganic material mounted upon a fixture, such inspection can be performed insitu. That is, the tip electrode of a catheter, substituted for electrode 80 and its support structure, can be passed across organic or inorganic material to develop signals reflective of the characteristics of the material. When the material is tissue, it is to be understood that any of the catheters described above usable in an invasive or non invasive procedure may be used in place of electrode 80 and its attendant structure illustrated in FIG. 14; it is to be understood that in such a procedure, electrode 82 and its attendant structure would be replaced by either plate 52 (see FIG. 5) or one or more of the ring electrodes of the catheter (see FIGS. 11a and 11b). Thus, it may be possible to map the boundaries of abnormal tissue (such as a tumor) or diseased tissue since such abnormal or diseased tissue will have boundaries that will be reflected in the change of characteristics sensed as the catheter passes across a line of demarcation between healthy and abnormal or diseased tissue. The type and nature of the abnormal and/or diseased tissue may also be identifiable as different tissues have different characteristics that can be sensed and quantified/qualified empirically. The resulting mapping of the tissue will provide to a physician unambiguous information that may be necessary to effectively perform a surgical or other procedure.

While the invention has been described with reference to several particular embodiments thereof, those skilled in the art will be able to make the various modifications to the described embodiments of the invention without departing from the true spirit and scope of the invention. It is intended that all combinations of elements and steps, which perform substantially the same function in substantially the same way to achieve the same results, are within the scope of the invention.

We claim:

1. Apparatus for combining two or more materials and determining on a real time basis the characteristics of the materials as such characteristics may change and of the characteristics of the resulting combined materials, said apparatus comprising in combination:
    a) a first source for applying energy to cause the combining of the materials;
    b) a second source for providing a monitor signal adapted to be applied to the materials to determine the characteristics of the materials on an ongoing basis;
    c) a circuit for sensing an initial and any real time change in said monitor signal as a function of the initial and any changes in the characteristics of the materials in response to the energy applied by said first source and for producing an ongoing output signal reflective of the characteristics of the materials and any changes thereof;
    d) a further circuit for correlating said monitor signal and said output signal to produce a first signal reflective of the magnitude of the impedance of the materials, a second signal reflective of the magnitude of the resistive component of the impedance of the materials and a third signal reflective of the magnitude of the reactive component of the impedance of the materials;
    e) an output device for providing indicia reflective of any or all of said first, second and third signals;
    f) a feedback circuit responsive to said output signal for controlling on an ongoing basis the level of energy applied by said first source; and
    g) processing apparatus for controlling operation of at least one of said first and second sources as a selected manual or automatic function of any of said first, second and third signals.

2. The apparatus as set forth in claim 1 including a radiation emitting element for irradiating the combined materials with energy and the monitor signal.

3. The apparatus as set forth in claim 2 including means for repositioning said element and materials relative to one another.

4. Apparatus for determining the characteristics of a material, said apparatus comprising in combination:
   a) a source for providing a monitor signal adapted to be applied to the material to determine the characteristics of the material on an ongoing basis;
   b) a circuit for continually sensing an initial and any ongoing change in said monitor signal as a function of any change of the characteristics of the material and for producing an ongoing output signal reflective of the characteristics;
   c) a further circuit for correlating said monitor signal and said output signal to produce a first signal reflective of the magnitude of the impedance of the material, a second signal reflective of the magnitude of the resistive component of the impedance of the material and a third signal reflective of the magnitude of the reactive component of the impedance of the material;
   d) an output device for providing indicia reflective of any or all of said first, second and third signals; and
   e) processing apparatus for controlling operation of said source as a selected manual or automatic function of any of said first, second and third signals.

5. The apparatus as set forth in claim 4 including a radiation emitting element for irradiating the material with the monitor signal.

6. A method for determining on a real time basis the characteristics of a material for a selected time period, said method comprising the steps of:
   a) providing a monitor signal adapted to be applied to the material to determine the characteristics of the material on an ongoing basis;
   b) sensing on a continuing real time basis any change in the monitor signal for the selected time period as a function of the initial and any ongoing change of the characteristics of the material and providing an ongoing output signal reflective of the characteristics of the material and any ongoing changes thereof;
   c) correlating the monitor signal and the output signal to produce a first signal reflective of the magnitude of the impedance of the material, a second signal reflective of the magnitude of the resistive component of the impedance of the material and a third signal reflective of the magnitude of the reactive component of the impedance of the material;
   d) displaying indicia reflective of any or all of the first, second and third signals; and
   e) controlling operation of said step of providing as a selected manual or automatic function of any of the first, second and third signals.

7. The method as set forth in claim 6 including and element for carrying out the step or irradiating the material with the monitor signal.

8. The method as set forth in claim 7 including the step of repositioning the element and the material relative to one another.

9. Apparatus for combining two or more materials and determining on a real time basis the characteristics of the materials and of the resulting combined materials, said apparatus comprising in combination:
   a) a first source for applying continuing energy to the materials until termination for causing the combining of the materials;
   b) a second source for providing a monitor signal adapted to be applied to the materials to determine the initial and any ongoing change of the characteristics of the materials;
   c) a circuit for sensing an initial and any real time change in said monitor signal as a function of the initial and changing characteristics of the materials and for producing an output signal reflective of the initial and any ongoing change of the characteristics;
   d) a further circuit for correlating said monitor signal and said output signal to produce a first signal reflective of the magnitude of the impedance of the materials, a second signal reflective of the magnitude of the resistive component of the impedance of the materials and a third signal reflective of the magnitude of the reactive component of the impedance of the materials;
   e) an output device for providing indicia reflective of any or all of said first, second and third signals; and
   f) processing apparatus for controlling operation of at least one of said first and second sources as a selected manual or automatic function of any of said first, second and third signals.

10. The apparatus as set forth in claim 9 including a radiation emitting element for irradiating the materials with energy from said first source.

11. The apparatus as set forth in claim 10 including means for repositioning said element and the materials relative to one another.

12. Apparatus for determining the characteristics of a material, said apparatus comprising in combination:
    a) a source for providing a continuing monitor signal applied to the material until terminated to determine the initial and any change in the characteristics of the material;
    b) a circuit for sensing on an ongoing basis an initial value and any change in value of said monitor signal as a function of the initial characteristics of the material any ongoing change of the characteristics of the material and for producing an output signal reflective of the initial and ongoing characteristics of the material;
    c) a further circuit for correlating said monitor signal and said output signal to produce a first signal reflective of the magnitude of the impedance of the material, a second signal reflective of the magnitude of the resistive component of the impedance of the material and a third signal reflective of the magnitude of the reactive component of the impedance of the material;
    d) an output device for providing indicia reflective of any or all of said first, second and third signals; and
    e) processing apparatus for controlling operation of said source as a selected manual or automatic function of any of said first, second and third signals.

13. The apparatus as set forth in claim 12 including a radiation emitting element for irradiating the material with the monitor signal.

14. The apparatus as set forth in claim 13 including means for repositioning said element and the material relative to one another.

15. A method for determining on a real time basis the characteristics of a material for a selected time period, said method comprising the steps of:
    a) providing a continuing monitor signal adapted to be applied to the material until terminated to determine the initial characteristics of the material and any ongoing change of the characteristics of the material;

b) sensing on a real time basis any change in the monitor signal for the selected time period as a function of any initial and ongoing change of the characteristics of the material and providing an output signal reflective of the initial and ongoing characteristics of the material;

c) correlating the monitor signal and the output signal to produce a first signal reflective of the magnitude of the impedance of the material, a second signal reflective of the magnitude of the resistive component of the impedance of the material and a third signal reflective of the magnitude of the reactive component of the impedance of the material;

d) displaying indicia reflective of any or all of the first, second and third signals; and e) controlling operation of said step of providing as a selected manual or automatic function of any of the first, second and third signals.

16. The method as set forth in claim 15 including an element for carrying out a step of irradiating the material with the monitor signal.

17. The method as set forth in claim 16 including the step of repositioning the element and the material relative to one another.

18. Apparatus for combining two or more materials and determining on a real time basis the characteristics of the materials and of the resulting combined materials, said apparatus comprising in combination:

a) a first source for applying energy adapted to cause the combining of the materials;

b) a second source for providing a monitor signal adapted to be applied to the materials to determine the initial characteristics of the materials and ongoing changes of the characteristics of the materials due to any temperature changes and any physical changes of the materials;

c) a circuit for sensing an initial and any ongoing real time change in said monitor signal as a function of the initial and ongoing changing characteristics of the materials and for producing an output signal reflective of the initial and ongoing characteristics of the materials;

d) a further circuit for correlating said monitor signal and said output signal to produce a first signal reflective of the magnitude of the impedance of the materials, a second signal reflective of the magnitude of the resistive component of the impedance of the materials and a third signal reflective of the magnitude of the reactive component of the impedance of the materials;

e) an output device for providing indicia reflective of any or all of said first, second and third signals;

f) a feedback circuit responsive to said output signal for controlling the level of energy of said first source; and g) processing apparatus for controlling operation of at least one of said first and second sources as a selected manual or automatic function of any of said first, second and third signals.

19. A method for combining two or more materials and determining on a real time basis the characteristics of the materials and of the resulting combined materials, said method comprising the steps of:

a) applying from a first source energy adapted to cause the combining of the materials;

b) providing from a second source a monitor signal adapted to be applied to the materials to determine the initial characteristics of the materials and ongoing changes of the characteristics of the materials due to any temperature changes and any physical changes of the materials;

c) sensing an initial and any ongoing real time change in the monitor signal as a function of the initial and ongoing changing characteristics of the materials and the step of producing an output signal reflective of the initial and ongoing characteristics of the materials;

d) correlating the monitor signal and the output signal to produce a first signal reflective of the magnitude of the impedance of the materials, a second signal reflective of the magnitude of the resistive component of the impedance of the materials and a third signal reflective of the magnitude of the reactive component of the impedance of the materials;

e) further providing indicia reflective of any or all of the first, second and third signals;

f) controlling the level of energy of the first source with a feedback circuit responsive to the output signal; and g) controlling operation of at least one of the first and second sources as a selected manual or automatic function of any of the first, second and third signals.

* * * * *